United States Patent
Tani et al.

(10) Patent No.: US 6,835,752 B2
(45) Date of Patent: Dec. 28, 2004

(54) CARBOXYLIC ACID DERIVATIVES, PROCESSES FOR THE PREPARATION THEREOF AND PHARMACEUTICAL AGENTS COMPRISING THE SAME AS ACTIVE INGREDIENT

(75) Inventors: Kousuke Tani, Mishima-gun (JP); Masaki Asada, Mishima-gun (JP); Kaoru Kobayashi, Mishima-gun (JP); Masami Narita, Mishima-gun (JP); Mikio Ogawa, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/344,989

(22) PCT Filed: Aug. 20, 2001

(86) PCT No.: PCT/JP01/07104

§ 371 (c)(1),
(2), (4) Date: Feb. 20, 2003

(87) PCT Pub. No.: WO02/16311

PCT Pub. Date: Feb. 28, 2002

(65) Prior Publication Data

US 2003/0216381 A1 Nov. 20, 2003

(30) Foreign Application Priority Data

Aug. 22, 2000 (JP) ........................................ 2000-251365

(51) Int. Cl.$^7$ ..................... C07C 233/43; A61K 31/165
(52) U.S. Cl. ........................................ 514/563; 562/433
(58) Field of Search .......................... 514/563; 562/433

(56) References Cited

FOREIGN PATENT DOCUMENTS

| | | | |
|---|---|---|---|
| FR | 2164481 | * 8/1973 | .......... A61K/27/00 |
| JP | 62-44738 | 2/1987 | |
| JP | 2000-86657 | 3/2000 | |

OTHER PUBLICATIONS

International Search Report for PCT/JP01/07104 dated Dec. 11, 2001.

* cited by examiner

*Primary Examiner*—Zinna Northington Davis
(74) *Attorney, Agent, or Firm*—Sughrue Mion, PLLC

(57) ABSTRACT

A carboxylic acid derivative of formula (1)

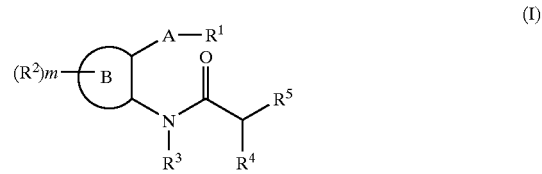

(I)

wherein $R^1$ is COOH, COOR$^6$ etc.; A is alkylene etc.; $R^2$ is alkyl, alkenyl, alkynyl etc.; B is carbocyclic ring or heterocyclic ring; $R^4$ is alkyl, cycloalkyl etc.; $R^6$ is carbocyclic ring or heterocyclic ring;

or non-toxic salts thereof, a process for the preparation thereof and a pharmaceutical agent comprising the same as active ingredient.

The compound of the formula (I) can bind to Prostaglandin $E_2$ receptors, especially, $EP_3$ receptor and/or $EP_4$ receptor and show the antagonizing activity, and useful for the prevention and/or treatment of disease, for example, pain, allergy, Alzheimer's disease, cancer.

5 Claims, No Drawings

CARBOXYLIC ACID DERIVATIVES, PROCESSES FOR THE PREPARATION THEREOF AND PHARMACEUTICAL AGENTS COMPRISING THE SAME AS ACTIVE INGREDIENT

TECHNICAL FIELD

The present invention relates to carboxylic acid derivatives. More specifically, the present invention relates to a carboxylic acid derivative of formula (I)

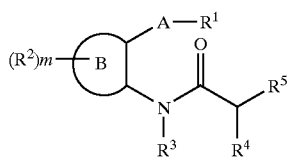

wherein all symbols are as hereinafter defined, a process for the preparation thereof and a pharmaceutical agent comprising the same as active ingredient.

BACKGROUND

Prostaglandin $E_2$ ($PGE_2$) has been known as a metabolite in the arachidonic acid cascade. It has been known that $PGE_2$ possesses cyto-protective activity, uterine contractile activity, a pain-inducing effect, a promoting effect on digestive peristalsis, an awaking effect, a suppressive effect on gastric acid secretion, hypotensive activity, and diuretic activity.

In the recent study, it was found that $PGE_2$ receptor was divided into some subtypes, which possesses different physical roles from each other. At present, four receptor subtypes are known and they are called $EP_1$, $EP_2$, $EP_3$ and $EP_4$ respectively (J. Lipid Mediators Cell Signaling 12, 379–391 (1995)).

Among these subtypes, $EP_a$ receptor was believed to be involved in signal transduction of peripheral nerve, control of exothermal reaction in central nerve, formation of memory by expressing in cerebral neuron, vascularization, reabsorption of urine by expressing in renal tubular, uterine contraction, production of ACTH, platelet aggregation. Besides, it was expressed in vascular smooth muscle, heart and gastrointestinal tract also. $EP_4$ recptor was believed to be involved in suppression of TNF-α production and induction of IL-10 production.

So the compounds which can bind to $EP_3$ receptor and/or $EP_4$ receptor strongly and show the antagonizing activity, are useful for the prevention and/or treatment of diseases induced by excess activation of $EP_3$ receptor and/or $EP_4$ receptor, for example, pain such as cancerous pain, fractural pain, pain following surgical and dental procedures; allodynia, hyperalgesia, pruritus, urticaria, atopic dermatitis, contact dermatitis, allergic conjunctivitis, various symptoms by treating with dialysis, asthma, rhinitis, sneeze, urinary frequency, neurogenic bladder, urinary disturbance, ejaculatory failure, defervescence, systemic inflammatory response syndrome, learning disturbance, Alzheimer's disease, cancer such as formulation of cancer, growth of cancer and metastasis of cancer; retinopathy, patch of red, scald, burn, burn by steroid, renal failure, nephropathy, acute nephritis, chronic nephritis, abnormal blood levels of electrolytes, threatened premature delivery, abortion threatened, hypermenorrhea, dysmenorrhea, uterine fibroids, premenstrual syndrome, reproductive disorder, stress, anxiety disorders, depression, psychosomatic disorder, mental disorder, thrombosis, embolism, transient ischemia attack, cerebral infarction, atheroma, organ transplant, myocardial infarction, cardiac failure, hypertension, arteriosclerosis, circulatory failure and circulatory failure induced ulcer, neuropathies, vascular dementia, edema, various arthritis, rheumatism, diarrhea, constipation, disorder of bilious excretion, ulcerative colitis, Crohn's disease and/or bone diseases such as osteoporosis, rheumatoid arthritis, osteoarthritis, abnormal bone formation; cancer such as formation of cancer, proliferation of cancer, metastasis of cancer to organs and to bones and hypercalcemia induced metastasis to bones of cancer; systemic granuloma, immunological diseases such as ALS, multiple sclerosis, Sjoegren's syndrome, systemic lupus erythematosus, AIDS; allergy such as conjunctivitis, rhinitis, contact dermatitis, psoriasis; atopic dermatitis, asthma, pyorrhea, gingivitis, periodontitis, neuronal cell death, Alzheimer's disease's disease, pulmonary injury, hepatopathy, acute hepatopathy, nephritis, renal failure, myocardial ischemia, Kawasaki disease, scald, ulcerative colitis, Crohn's disease, multiple organ failure etc. Moreover, $EP_4$ is thought to be involved in sleeping disorder and platelet aggregation, so the compounds are considered to be useful.

DISCLOSURE OF THE INVENTION

The present inventors have energetically studied to find the compound which bind to $PGE_2$ receptor, $EP_3$ and/or $EP_4$ receptor specifically and show an inhibitory activity against it, to find out that the carboxylic acid derivatives of formula (I) achieve the purpose and completed the present invention.

This invention was relates to (1) a carboxylic acid derivative of formula (I)

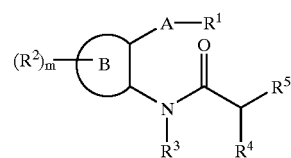

wherein $R^1$ is COOH, $COOR^6$, $CH_2OH$, $CONHSO_2R^7$ or $CONR^8R^9$, $R^6$ is C1–6 alkyl, (C1–4 alkylene)—$R^{16}$, $R^7$ is (1) C1–4 alkyl, or (2) substituted by 1–2 of substitutes selected form C1–4 alkyl, C1–4 alkoxy and halogen atom or unsubstituted (2–1) C6–12 mono- or bi-carbocyclic ring or (2-2) 5–15 membered mono- or bi-heterocyclic ring containing at least one of hetero atom selected from nitrogen, oxygen and sulfur, or (3) C1–4 alkyl substituted by the above substituents or unsubstituted carbocyclic ring or heterocyclic ring, $R^8$ and $R^9$ each independently, is hydrogen or C1–4 alkyl, $R^{16}$ is hydroxy, C1–4 alkoxy, COOH, C1–4 alkoxycarbonyl, $CONR^8R^9$, A is C1–6 alkylene or —(C1–3 alkylene)$_w$—G—(C1–3 alkylene)—, w is 0 or 1, G is oxygen, sulfur or $NR^{10}$, $R^{10}$ is hydrogen or C1–4 alkyl, $R^2$ is C1–6 alkyl, C2–6 alkenyl, C2–6 alkynyl, C1–6 alkoxy, halogen atom, $CF_3$, cyano, nitro, hydroxy, $NR^{11}R^{12}$, $CONR^{11}R^{12}$, $SO_2NR^{11}R^{12}$, or —S(O)$_x$—(C1–6)alkyl, m is 0, 1 or 2, when m is 2, then two $R^2$ may be same or difference, $R^{11}$ and $R^{12}$ each independently, hydrogen or C1–4 alkyl, x is 0, 1 or 2, B ring is C5–7 mono-carbocyclic ring or 5–7 membered mono-heterocyclic ring containing at least one of nitrogen, oxygen and sulfur, $R^3$ is hydrogen or C1–4 alkyl, $R^4$ is (1) C1–8 alkyl, (2) C2–8 alkenyl, (3) C2–8 alkynyl, (4) C3–6 cycloalkyl, (5) hydroxy, (6) C1–4 alkoxy, (7) C1–4 alkoxy(C1–4)alkoxy, or (8) C1–8 alkyl substituted by 1–2 of substitutes selected from halogen atom, hydroxy, C1–6 alkoxy, C1–4 alkoxy(C1–4)alkoxy, phenyl and C3–6 cycloalkyl, $R^5$ is substituted by 1–2 of $R^{13}$ or unsubstituted C5–10 mono- or bi-carbocyclic ring or 5–10 membered mono- or bi-heterocyclic ring containing at least one of nitrogen, oxygen and sulfur, $R^{18}$ is C1–6 alkyl, C1–6 alkoxy, halogen atom, $CF_3$, cyano, C1–4 alkoxy(C1–4)alkyl, phenyl, phenyl(C1–6) alkyl, —(C1–4 alkylene)$_y$-J—(C1–8 alkylene)$_x$—$R^{14}$, benzoyl or thiophenecarbonyl and two $R^{13}$ may be same or difference, y is 0 or 1, z is 0 or 1, $R^{14}$ is phenyl or pyridyl, J is oxygen, $S(O)_t$ or $NR^{15}$, t is 0, 1 or 2, $R^{16}$ is hydrogen, C1–4 alkyl or acetyl;

or non-toxic salts, (2) a process of the preparation thereof, and (3) a pharmaceutical agent comprising the same as active ingredient.

DETAILED DESCRIPTION OF THE INVENTION

In the present invention, C1–4 alkyl is methyl, ethyl, propyl, butyl and isomers thereof.

In the present invention, C1–6 alkyl is methyl, ethyl, propyl, butyl, pentyl, hexyl and isomers thereof.

In the present invention, C1–8 alkyl is methyl, ethyl, propyl, butyl, pentyl, hexyl, heptyl, octyl and isomers thereof.

In the present invention, C2–6 alkenyl is ethenyl, propenyl, butenyl, pentenyl, hexenyl and isomers thereof.

In the present invention, C2–8 alkenyl is ethenyl, propenyl, butenyl, pentenyl, hexenyl, heptenyl, octenyl and isomers thereof.

In the present invention, C2–6 alkynyl is ethynyl, propynyl, butynyl, pentynyl, hexynyl and isomers thereof.

In the present invention, C2–8 alkynyl is ethynyl, propynyl, butynyl, pentynyl, hexynyl, heptynyl, octynyl and isomers thereof.

In the present invention, C1–4 alkoxy is methoxy, ethoxy, propoxy, butoxy and isomers thereof.

In the present invention, C1–6 alkoxy is methoxy, ethoxy, propoxy, butoxy, pentyloxy, hexyloxy and isomers thereof.

In the present invention, C1–4 alkoxy(C1–4)alkyl is, for example, methoxymethyl, methoxyethyl, methoxypropyl, methoxybutyl, ethoxymethyl, ethoxyethyl, ethoxypropyl, ethoxybutyl, propoxymethyl butoxymethyl and isomers thereof.

In the present invention, C1–4 alkoxy(C1–4)alkoxy is, for example, methoxymethoxy, methoxyethoxy, methoxypropoxy, methoxybutoxy, ethoxymethoxy, ethoxyethoxy, ethoxypropoxy, ethoxybutoxy and isomers thereof.

In the present invention, C1–4 alkoxycarbonyl is methoxycarbonyl, ethoxycarbonyl, propoxycarbonyl, butoxycarbonyl and isomers thereof.

In the present invention, C1–2 alkylene is methylene, ethylene and isomers thereof.

In the present invention, C1–3 alkylene is methylene, ethylene, trimethylene and isomers thereof.

In the present invention, C1–4 alkylene is methylene, ethylene, trimethylene, tetramethylene and isomers thereof.

In the present invention, C1–6 alkylene is methylene, ethylene, trimethylene, tetramethylene, pentamethylene, hexamethylene and isomers thereof.

In the present invention, C1–8 alkylene is methylene, ethylene, trimethylene, tetramethylene, pentamethylene, hexamethylene, heptamethylene, octamethylene and isomers thereof.

In the present invention, C2–4 alkylene is ethylene, trimethylene, tetramethylene and isomers thereof.

In the present invention, C3–6 cycloalkyl is cyclopropyl, cyclobutyl, cyclopentyl, and cyclohexyl.

In the present invention, halogen atom is fluoride, chloride, bromide and iodide.

In the present invention, C6–12 mono- or bi-carbocyclic ring is C6–12 unsaturated, or partially or fully saturated mono- or bi-carbocyclic ring, for example, cyclohexane, cycloheptane, cyclohexene, benzene, indene, naphthalene, indan, tetrahydronaphthalene.

In the present invention, 5–15 membered mono- or bi-heterocyclic ring containing at least one of hetero atom selected from nitrogen, oxygen and sulfur is 5–15 membered unsaturated, or partially or fully saturated mono- or bi-heterocyclic ring containing 1–4 of nitrogen(s), 1–2 of oxygen(s), 1 of sulfur, 1 of nitrogen and 1 of oxygen, or 1 of nitrogen and 1 of sulfur, for example, furan, thiophene, pyrrole, oxazole, isoxazole, isothiazole, imidazole, pyrazole, tetrazole, pyridine, pyrimidine, pyrazine, benzofuran, benzothiophene, benzothiazole, indole, benzoxazole, benzimidazole, benzodioxane, thienopyridine, indoline, isoindoline, 1,3-dioxaindan, chroman, isochroman, quinoline, isoquinoline, quinazoline, quinoxaline.

In the present invention, C5–7 mono-carbocyclic ring is C5–7 unsaturated, partially or fully saturated mono-carbocyclic ring, for example, cyclopentane, cyclohexane, cycloheptane, cyclopentene, cyclohexene, benzene.

In the present invention, 5–7 membered mono-heterocyclic ring containing at least one of hetero atom selected from nitrogen, oxygen and sulfur is 5–7 membered mono-heterocyclic ring containing 1–2 of nitrogen(s), 1–2 of oxygen(s) and/or 1 of sulfur, for example, furan, thiophene, pyrrole, oxazole, isoxazole, thiazole, isothiazole, imidazole, pyridine, pyrimidine, pyrazine, azepine.

In the present invention, C5–6 mono-carbocyclic ring is C5–6 unsaturated, partially or fully saturated mono-carbocyclic ring, for example, cyclopentane, cyclohexane, cyclopentene, cyclohexene, benzene.

In the present invention, 5–6 membered mono-heterocyclic ring containing 1–2 of nitrogen(s), 1 of oxygen and/or 1 of sulfur, for example, furan, thiophene, pyrrole, oxazole, isoxazole, thiazole, isothiazole, imidazole, pyridine, pyrimidine, pyrazine.

In the present invention, C5–10 mono- or bi-carbocyclic ring is C5–10 unsaturated, partially or fully saturated mono- or bi-carbocyclic ring, for example, cyclopentane, cyclohexane, cycloheptane, benzene, indan, indene, naphthalene, and tetrahydronaphthalene.

In the present invention, 5–10 membered mono- or bi-heterocyclic ring containing at least one of hetero atom selected from nitrogen, oxygen and sulfur is 5–10 membered unsaturated, partially or fully saturated mono- or bi-heterocyclic ring containing 1–4 of nitrogen(s), 1–2 of oxygen(s), 1 of sulfur, 1 of nitrogen and 1 of oxygen or 1 of nitrogen and 1 of sulfur, for example, furan, thiophene, pyrrole, oxazole, isoxazole, thiazole, isothiazole, imidazole, pyrazole, tetrazole, pyridine, pyrimidine, pyrazine, benzofuran, benzothiophene, benzothiazole, indole, benzoxazole, benzimidazole, benzodioxane, thienopyridine, indoline, isoindoline, 1,3-dioxaindane, chroman, isochroman, quinoline, isoquinoline, quinazoline, quinoxaline.

In the present invention, 5–10 membered mono- or bi-heterocyclic ring containing 1–2 of nitrogen(s), 1–2 of oxygen(s) and/or 1 of sulfur is 5–10 membered unsaturated, partially or fully saturated mono- or bi-heterocyclic ring containing 1–2 of nitrogen(s), 1–2 of oxygen(s), 1 of sulfur, 1 of nitrogen and 1 of oxygen or 1 of nitrogen and 1 of sulfur, for example, furan, thiophene, pyrrole, oxazole, isoxazole, thiazole, isothiazole, imidazole, pyrazole, pyridine, pyrimidine, pyrazine, benzofuran, benzothiophene, benzothiazole, indole, benzoxazole, benzoimidazole, benzodioxane, indoline, isoindoline, 1,3-dioxaindane, chroman, isochroman, quinoline, isoquinoline, quinazoline, quinoxaline.

Unless otherwise specified, all isomers are included in the present invention. For example, alkyl, alkenyl, alkynyl and alkylene groups include straight-chain and also branched-chain ones. In addition, isomers in double bond, ring, fused ring (E-, Z-, cis-, trans-isomer), isomers generated from asymmetric carbon atom(s) (R-, S-, α-, β-isomer, enantiomer, diastereomer), optically active isomers having optical rotation (D-, L-, d-, l-isomer), polar compounds separated by chromatography (more polar compound, less polar compound), equilibrium compounds, mixtures thereof at arbitrary ratios and racemic mixtures are included in the present invention.

More preferably compound of the present invention of formula (1) is the compound which is $R^1$ is COOH, COOR$^6$, CH$_2$OH, CONHSO$_2$R$^7$ or CONR$^8$R$^9$, $R^6$ is C1–6 alkyl, (C1–4 alkylene)—R$^{16}$, $R^7$ is (1) C1–4 alkyl, or (2) substituted by 1–2 of substitutes selected form C1–4 alkyl, C1–4 alkoxy and halogen atom or unsubstituted (2-1) C6–12 mono- or bi-carbocyclic ring or (2-2) 5–15 membered mono- or bi-heterocyclic ring containing at least one of hetero atom selected from nitrogen, oxygen and sulfur, or (3) C1–4 alkyl substituted by the above substituted or unsubstituted carbocyclic ring or heterocyclic ring, $R^8$ and $R^9$ each independently, is hydrogen or C1–4 alkyl, $R^{10}$ is hydroxy, C1–4 alkoxy, COOH, C1–4 alkoxycarbonyl, CON$^8$R$^9$, A is C2–4 alkylene or —(C1–2 alkylene)$_w$-G—(C1–2 alkylene)-, w is 0 or 1, G is oxygen, sulfur or NR$^{10}$, $R^{10}$ is hydrogen or C1–4 alkyl, $R^2$ is C1–6 alkyl, C2–6 alkenyl, C2–6 alkynyl, C1–6 alkoxy, halogen atom, CF$_3$ or cyano, B ring is C5–6 mono-carbocyclic ring or 5–6 membered mono-heterocyclic ring containing 1–2 of nitrogen(s), 1 of oxygen and/or 1 of sulfur, m is 0 or 1, $R^3$ is hydrogen or C1–4 alkyl, $R^4$ is C1–8 alkyl, C3–6 cycloalkyl or C1–8 alkyl substituted by 1–2 of C3–6 cycloalkyl, $R^5$ is substituted by 1–2 of $R^{13}$ or unsubstituted, C5–10 mono- or bi-carbocyclic ring or 5–10 membered mono- or bi-heterocyclic ring containing 1–2 of nitrogen(s), 1–2 of oxygen(s) and/or 1 of sulfur, $R^{13}$ is C1–6 alkyl, C1–6 alkoxy, halogen atom, CF$_3$, cyano or —(C1–4 alkylene)$_y$-J—(C1–8 alkylene)$_z$—R$^{14}$, y is 0, J is oxygen, z is 1, $R^{14}$ is phenyl;

or non-toxic salts thereof.

In the present compound of formula (I), a preferably $R^1$ is COOH, COOR$^6$, CH$_2$OH, CONHSO$_3$R$^7$ or CONR$^8$R$^9$, in which a preferably $R^7$ is (1) C1–4 alkyl, (2) substituted by 1–2 of substitutes selected from C1–4 alkyl, C1–4 alkoxy and halogen atom, or unsubstituted cyclohexane, cycloheptane, cyclohexane, benzene, indene, naphthalene, indan, tetrahydronaphthalene, furan, thiophene, pyrrole, oxazole, isoxazole, thiazole, isothiazole, imidazole, pyrazole, tetrazole, pyridine, pyrimidine, pyrazine, benzofuran, benzothiophene, benzothiazole, indole, benzoxazole, benzoimidazole, benzodioxane, thienopyridine, indoline, isoindoline, 1,3-dioxaindan, chroman, isochroman, quinoline, isoquinoline, quinoxaline or (3) C1–2 alkyl substituted by the above ring described in (2), especially preferably $R^7$ is (1) C1–4 alkyl, (2) substituted by 1–2 of substitutes selected from C1–4 alkyl, C1–4 alkoxy and halogen atom, or unsubstituted benzene, thiophene, oxazole, isoxazole, thiazole, isothiazole, pyridine or (3) C1–2 alkyl substituted by the above ring described in (2), and the other symbols are as hereinbefore defined.

In the compound of the present invention, concrete B ring is cyclopentane, cyclohexane, cycloheptane, cyclopentene, cyclohexene, benzene, furan, thiophene, pyrrole, oxazole, isoxazole, thiazole, isothiazole, imidazole, pyridine, pyrimidine, pyrazine, and azepine. Preferably B ring is cyclopentane, cyclohexane, benzene, furan, thiophene, pyrrole, imidazole, pyridine, pyrimidine, pyrazine, especially preferably, cyclohexane, benzene, thiophene, pyridine.

In the compound of the present invention, concrete $R^5$ is substituted by 1–2 of $R^{13}$, wherein $R^{13}$ is as hereinbefore defined; or unsubstituted cyclopentane, cyclohexane, cycloheptane, benzene, indan, indene, naphthalene, tetrahydronaphthalene, furan, thiophene, pyrrole, oxazole, isoxazole, thiazole, isothiazole, imidazole, pyrazole, tetrazole, pyridine, pyrimidine, pyrazine, benzofuran, benzothiophene, benzothiazole, indole, benzoxazole, benzoimidazole, benzodioxane, thienopyridine, indoline, isoindoline, 1,3-dioxaindan, chroman, isochroman, quinoline, isoquinoline, quinazoline, quinoxaline. Preferably $R^5$ is substituted by 1–2 of $R^{13}$, wherein $R^{13}$ is as hereinbefore defined; or unsubstituted cyclohexane, benzene, naphthalene, tetrahydronaphthalene, furan, thiophene, pyrrole, pyridine, pyrimidine, pyrazine, benzofuran, benzothiophene, indole, benzodioxane, quinoline, isoquinoline, quinazoline, quinoxaline, especially preferably, substituted by 1–2 of $R^{13}$, wherein $R^{13}$ is as hereinbefore defined; or unsubstituted benzene, naphthalene, tetrahydronaphthalene, benzofuran, benzothiophene, indole, benzodioxane, quinoline.

In the compounds of the present invention of formula (I), the compounds described in examples are preferable.

Salt

The compound of the present invention of formula (I) may be converted into a corresponding salt by known methods. In the present invention, salts are salts of alkali metals, salts of alkaline-earth metals, ammonium salts, pharmaceutically acceptable organic amines, acid addition salts and hydrates. Non-toxic and water-soluble salts are preferable.

Appropriate salts are, salts of alkali metals such as potassium, sodium, etc.; salts of alkaline-earth metals such as calcium, magnesium, etc.; ammonium salts, pharmaceutically acceptable organic amines such as tetramethylammonium, triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.

Appropriate acid addition salts are, salts of inorganic acids such as hydrochloride, hydrobromide, sulfate, phosphate, nitrate; salts of organic acids e.g. acetate, trifluoroacetate, lactate, tartrate, oxalate, fumarate, maleate, citrate, benzoate, methanesulphonate, ethanesulphonate, benzenesulphonate, toluenesulphonate, isethionate, glucuronate, gluconate.

The compounds of formulae (I) and salts thereof may be converted into the corresponding hydrates by conventional means.

Preparation of the Compound of the Present Invention

The present compound of formula (a) may be prepared, for example, by the following method.

(1) In the compound of formula (I), wherein $R^1$ is COOH, that is the compound of formula (Ia)

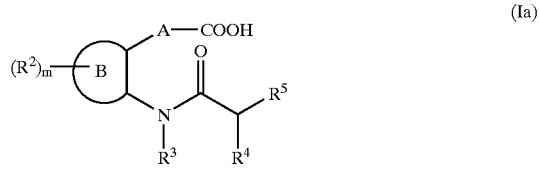

(Ia)

wherein all symbols are as hereinbefore defined;

may be prepared by subjecting to hydrolysis under an alkaline conditions the compound of formula (Ib-1)

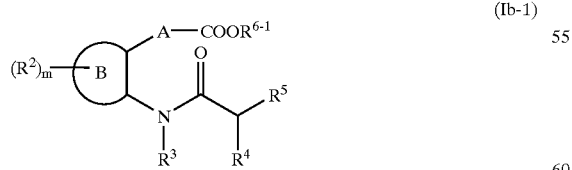

(Ib-1)

wherein $R^{6-1}$ is C1–6 alkyl and the other symbols are as hereinbefore defined.

Hydrolysis under alkaline conditions is known, for example, it is carried out in a water-miscible organic solvent (e.g. methanol, ethanol, tetrahydrofuran, dioxane or a mixture thereof), using an aqueous solution of an alkali (e.g. sodium hydroxide, potassium hydroxide or potassium carbonate) at $-10$–$90°$ C.

(2) In the compound of formula (I), wherein $R^1$ is $CH_2OH$, that is the compound of formula (Ic)

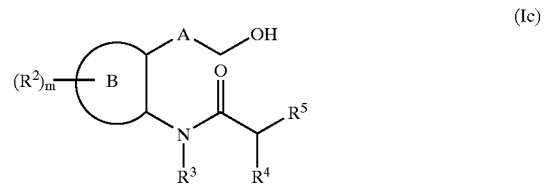

(Ic)

wherein all symbols are as hereinbefore defined;

may be prepared by subjecting to reduction the compound of formula (Ia).

Reduction reaction is known, for example, it is carried out in organic solvent (e.g. tetrahydrofuran, diglyme), using borane complex at 0–50° C.

(3) In the compound of formula (I), wherein $R^1$ is $CONHSO_2R^7$ and $CONR^8R^9$, that is the compound of formula (Id)

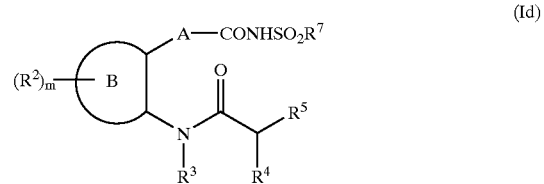

(Id)

wherein all symbols are as hereinbefore defined; and the compound of formula (Ie)

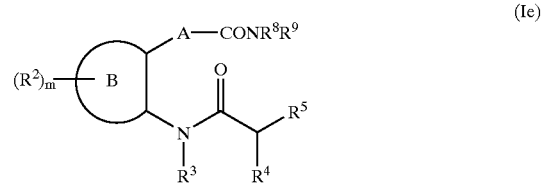

(Ie)

wherein all symbols are same as hereinbefore defied;

may be prepared by subjecting to amidation reaction the compound of formula (Ia) and the compound of formula (II-1)

$H_2NSO_2R^7$ (II-1)

wherein all symbols are as hereinbefore defined; or the compound of formula (II-2)

$HNR^8R^9$ (II-2)

wherein all symbols are as hereinbefore defined.

Amidation reaction is known, for example, it is carried out in an organic solvent (e.g. tetrahydrofuran, methylene chloride, chloroform, benzene, acetone, acetonitrile, diethyl ether or a mixture thereof), in the presence or absence of a tertiary amines (e.g. dimethylaminopyridine, pyridine, triethylamine), using a condensing agent (e.g. 1,3-dicyclohexylcarbodiimide(DCC), 1-ethyl-3-[3-(dimethylamino)propyl]carbodiimide(EDC), 2-chloro-1-methylpyridium iodide) or acyl halide (e.g. oxalyl chloride, thionyl chloride, phosphorus oxychloride) at 0–50° C.

(4) The compound of formula (Ib-1) may be prepared by subjecting to amidation reaction the compound of formula (III)

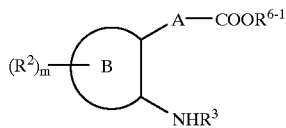
(III)

wherein all symbols are as hereinbefore defined; and the compound of formula (IV)

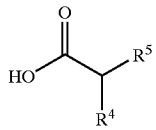
(IV)

wherein all symbols are as hereinbefore defined.

Amidation reaction is carried out by the above method.

(5) In the compound of formula (I), wherein $R^1$ is $COOR^{6-2}$, in which $R^{6-2}$ is —(C1–4 alkylene)-$R^{18}$; that is the compound of formula (Ib-2)

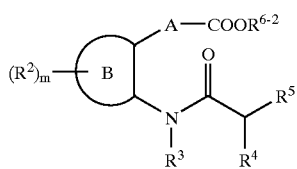
(Ib-2)

wherein all symbols are as hereinbefore defined; may be prepared by reacting the compound of formula (Ia) with the compound of formula (V)

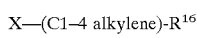
X—(C1–4 alkylene)-$R^{16}$ (V)

wherein X is halogen atom and the other symbols are as hereinbefore defined.

This reaction is known, for example, it is carried out in an organic solvent (e.g. dimethylformamide, tetrahydrofuran, acetone, acetonitrile), using potassium carbonate, sodium carbonate or sodium hydride, at 0–50° C.

The compounds of formula (II-1), (II-2), (III), (IV) and (V) may be known per se, or may be prepared by known methods with ease. For example, among the compound of formula (III), 4-(2-aminopheny)butyric acid methyl ester is described in the document of Synthetic Communications, 26(18), 3443–3452 (1996).

The compound of formula (III) may be prepared according to the following reaction scheme A. Besides, a part of the compound of formula (III) may be also prepared according to the following reaction scheme B.

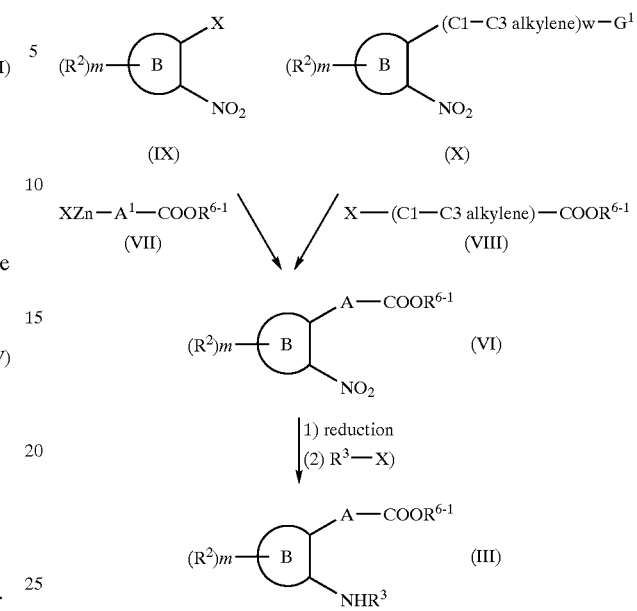

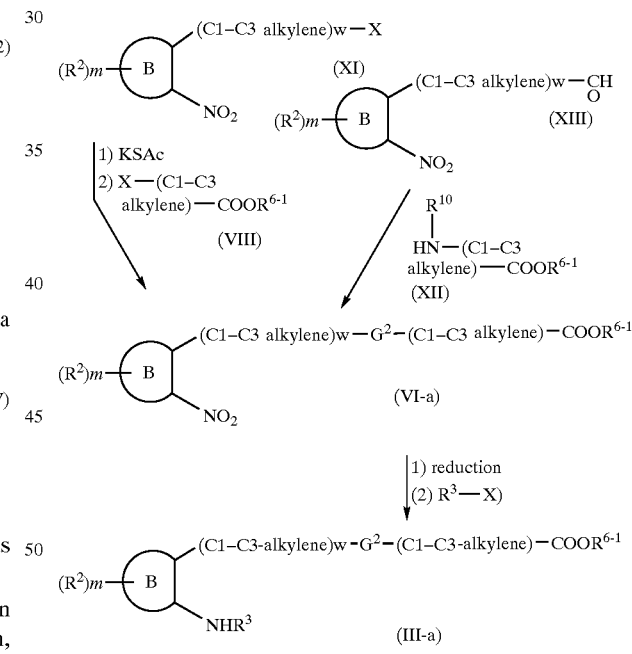

In above schemes $A^1$ is C1–6 alkylene, $G^1$ is OH, SH, $NHR^{10}$, $G^2$ is S, NR10, Ac is acetyl, the other symbols are as hereinbefore defined.

Besides, the compound of formula (I) may be also prepared according to the following reaction schemes C, D-1 or D-2.

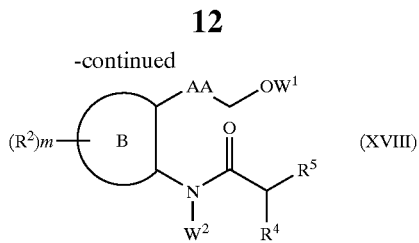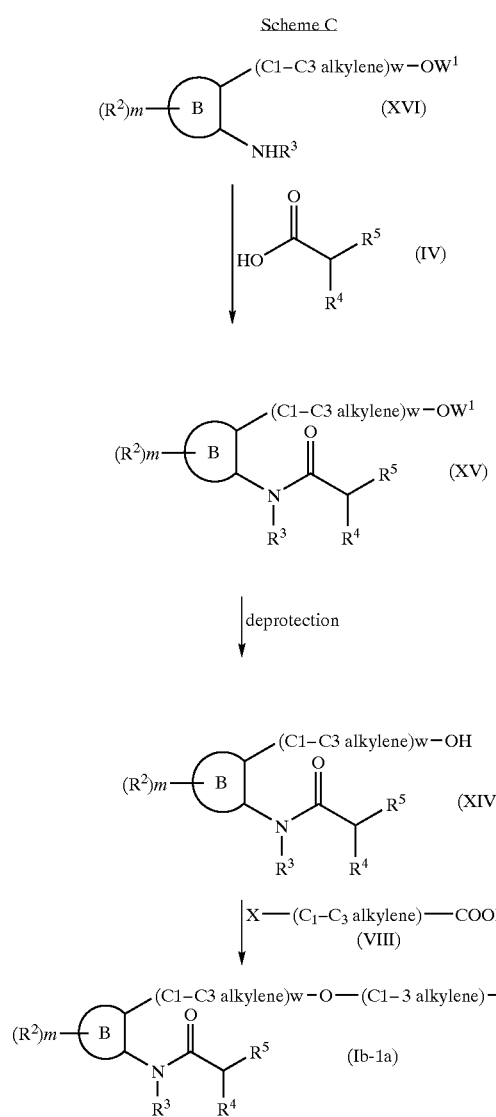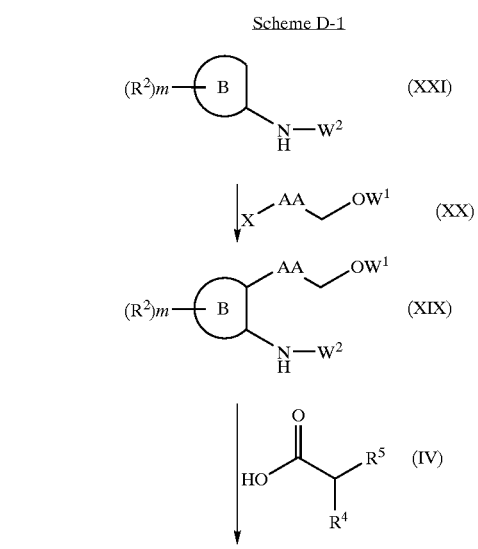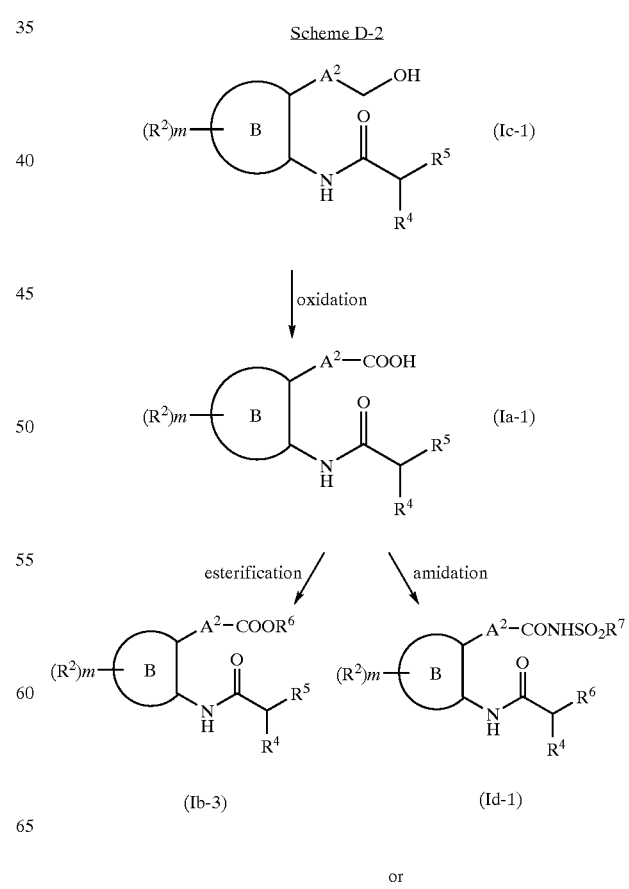

-continued

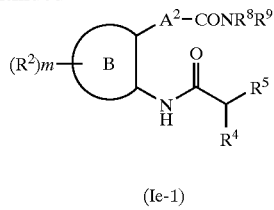

(Ie-1)

In above schemes
AA is C2–6 alkenylene,
$A^2$ is C2–6 alkylene,
$W^1$ is a protecting group of hydroxy,
$W^2$ is a protecting group of amino,
the other symbols are as hereinbefore defined.

And the starting materials and reagents may be known per se or may be prepared by known methods.

The desired compound having hydroxy or amino may be easily prepared by a corresponding method selected from deprotection reactions such as deprotection under alkaline conditions, deprotection under acidic conditions and hydrogenolysis, using the compound having protected hydroxy or protected amino by a corresponding protecting group.

Methoxymethyl, tetrahydopyranyl, t-butyldimethylsilyl, acetyl, benzyl may be used as protecting groups for hydroxy. As protecting groups, other groups, which can be removed easily and selectively other than the above protecting groups, are also preferred.

Benzyloxycarbonyl, t-butoxycarbonyl, trifluoroacetyl may be used as protecting groups for amino. As protecting groups, other groups, which can be removed easily and selectively other than the above protecting groups, are also preferred. For example, the groups described in T. W. Greene, Protective Groups in Organic Synthesis, Wiley, N.Y., 1991, may be used.

In each reaction in the present specification, reaction products may be purified by conventional purification techniques, e.g. by distillation under atmospheric or reduced pressure, by high performance liquid chromatography, by thin layer chromatography or by column chromatography using silica gel or magnesium silicate; or by washing or by recrystallization. Purification may be carried out after each reaction or after a series of reactions.

[Pharmacological Activities]

The compounds of the present invention of formula (I) bind strongly and show an antagonizing activity on the $PGE_2$ receptor, especially, $EP_3$ and/or $EP_4$ receptor.

For example, in a standard laboratory test, such effects of the compound of the present invention were confirmed by binding assay using the cell expressing the prostanoid receptor subtypes.

(i) Binding Assay Using Cell Expressing the Prostanoid Receptor Subtypes

The preparation of membrane fraction was carried out according to the method of Sugimoto et al [J. Biol. Chemical, 267, 6463–6466 (1992)], using CHO cell expressing prostanoid receptor subtypes (mouse $EP_1$, $EP_2$, $EP_{3\alpha}$, and $EP_4$).

The standard assay mixture containing membrane fraction (50 μL), [$^3$H]—$PGE_2$ in a final volume of 150 μL was incubated for 1 hour at room temperature. The reaction was terminated by addition of 3 mL of ice-cold buffer. The mixture was rapidly filtered through a glass filter (GF/B) under reduced pressure. The radioactivities associated with the filters were measured by liquid scintillation counter.

Kd and Bmax values were determined from Scatchard plots [Ann. N. Y. Acad. Sci. 51, 660(1949)]. Non-specific binding was determined as the amount bound in the presence of an excess (2.5 μM of unlabeled $PGE_2$. In the experiment for competition of specific [$^3$H]—$PGE_2$ binding assay, [$^3$H]—$PGE_2$, was added at a concentration of 2.5 nM and a test compound of the present invention was added at various concentrations. The following buffer was used in all reactions.

Buffer: 10 mM potassium phosphate (pH 6.0), 1 mM EDTA, 10 mM $MgCl_2$, 0.1 M NaCl.

The inhibition constant (Ki) (μM) of each compound was calculated by the following equation. The results are shown in Table 1.

$Ki=IC_{50}/(1+([C]/Kd))$

TABLE 1

| | $Ki(\mu M)$ | | | |
|---|---|---|---|---|
| Example No. | $EP_1$ receptor | $EP_2$ receptor | $EP_3$ receptor | $EP_4$ receptor |
| 2 | >10 | >10 | 2.4 | 0.3 |

(ii) $EP_3$ antagonizing activity assay using the cell expressing the prostanoid receptor subtypes The preparation of CHO cell expressing mouse $EP_3$ receptor subtype was carried out according to the method of Sugimoto et al [J. Biol. Chem. 267, 6463–6466 (1992)]. The cells were cultured in 96-well microplates ($10^4$ cells/well) for two days before experiments. After washing each well with 100 μL of PBS, Fura-2AM was added to taken in the cell for 60 mutes. After washing each well with HEPES, then a test compound and $PGE_2$ (10 nM) were added at 37° C. A variation of intracellular calcium concentration was measured. Namely, excitation with a wavelength of 340/380 nm carried out, and fluorescence of 510 nm was measured, then a ratio of fluorescence intensity was calculated. By the way, an antagonizing activity of a test compound was calculated as inhibitory rate on the condition using $PGE_2$ (10 nM) as an agonist, and then $IC_{50}$ value was calculated.

(ii) $EP_4$ Antagonizing Activity Assay Using the Cell Expressing the Prostanoid Receptor Subtypes The preparation of CHO cell expressing mouse $EP_4$ receptor subtype was carried out according to the method of Nishigaki et al [FEBS lett., 364, 339–341(1995)]. The cells were cultured in 24well microplates ($10^5$ cells/well) for two days before experiments. After washing each well with 500 μL of MEM (MEM essential medium), thereto was added 450 μL of assay medium MEM containings 1 mmol/L IBMX, 1% BSA), and the mixture was incubated for 10 minutes at 37° C. Then $PGE_2$ alone or a combination with a test compound (50 μL) were added, and the mixture was incubated for 10 minutes at 37° C. And reaction was terminated by addition of ice-cold TCA (10% w/v, 500 μL). This reaction mirture was freezed once (-80° C.) and thawed, and cells were harvested using a scraper. After centrifugation (13,000 r.p.m., for 3 minutes), cAMP content was measured using cAMP assay kit. That is, the supernatant (125 μL) was diluted with 500 μL of [$^{125}$I]-cAMP assay kit buffer (Amersham), and mixed with 0.5 mol/L tri-n-octylamine/chloroform solution (1 mL) was med. After removal of TCA from chloroform layer, cAMP content in the aqueous layer was quantified according to the method of kit manuals.

An antagonizing activity of compound ($IC_{50}$ value) was calculated as an inhibitory rate on the condition using 100 nM $PGE_2$ as an agonist. This concentration of $PGE_2$ served a submaximal effect on cAMP production.

As mentioned above, it was clear that the compounds of the present invention show a strong antagonizing activity on the $EP_3$ and/or $EP_4$ subtype receptor.

[Toxicity]

The toxicity of the compounds of the formula (I) of the present invention is very low and therefore, it is confirmed that these compounds are safe for use as medicine.

[Application to Pharmaceuticals]

The compounds of the present invention of the formula (I) can bind and show the antagonizing activity on the $PGE_2$ receptor. Particularly, they bind to $EP_3$ receptor and/or $EP_4$ receptor strongly and show the antagonizing activity, are useful for the prevention and/or treatment of diseases induced by excess activation of $EP_3$ receptor and/or $EP_4$ receptor, for example, pain such as pain such as cancerous pain, fractural pain, pain following surgical and dental procedures; allodynia, hyperalgesia, pruritus, urticaria, atopic dermatitis, contact dermatitis, allergic conjunctivitis, various symptoms by treating with dialysis, asthma, rhinitis, sneeze, urinary frequency, neurogenic bladder, urinary disturbance, ejaculatory failure, defervescence, systemic inflammatory response syndrome, learning disturbance, Alzheimer's disease, cancer such as formulation of cancer, growth of cancer and metastasis of cancer; retinopathy, patch of red, scald, burn, burn by steroid, renal failure, nephropathy, acute nephritis, chronic nephritis, abnormal blood levels of electrolytes, threatened premature delivery, abortion threatened, hypermenorrhea, dysmenorrhea, uterine fibroids, premenstrual syndrome, reproductive disorder, stress, anxiety disorders, depression, psychosomatic disorder, mental disorder, thrombosis, embolism, transient ischemia attack, cerebral infarction, atheroma, organ transplant, myocardial infarction, cardiac failure, hypertension, arteriosclerosis, circulatory failure and circulatory failure induced ulcer, neuropathies, vascular dementia, edema, various arthritis, rheumatism, diarrhea, constipation, disorder of bilious excretion, ulcerative colitis, Crohn's disease and/or bone diseases such as osteoporosis, rheumatoid arthritis, osteoarthritis, abnormal bone formation; cancer such as formation of cancer, proliferation of cancer, metastasis of cancer to organs and to bones and hypercalcemia induced metastasis to bones of cancer; systemic granuloma, immunological diseases such as ALS, multiple sclerosis, Sjoegren's syndrome, systemic lupus erythematosus, AIDS; allergy such as conjunctivitis, rhinitis, contact dermatitis, psoriasis; atopic dermatitis, asthma, pyorrhea, gingivitis, periodontitis, neuronal cell death, Alzheimer's disease's disease, pulmonary injury, hepatopathy, acute hepatopathy, nephritis, renal failure, myocardial ischemia, Kawasaki disease, scald, ulcerative colitis, Crohn's disease, multiple organ, sleeping disorder and platelet aggregation.

For the purpose described above, the compounds of formula (I), of the present invention, non-toxic salts thereof may be normally administered systemically or topically, usually by oral or parenteral administration.

The doses to be administered are determined depending upon, for example, age, body weight, symptom, the desired therapeutic effect, the route of administration, and the duration of the treatment, etc. In the human adult, the doses per person at a time are generally from 0.1 mg to 100 mg, by oral administration, up to several times per day, and from 0.01 mg to 10 mg, by parenteral administration (preferably intravenous administration), up to several times per day, or continuous administration between 1 and 24 hours per day into vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules.

In such solid forms, one or more of the active compound(s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, physiological salt solution, vegetable oil, propylene glycol, polyethylene glycol, alcohol, e.g. ethanol, or a mixture thereof.

Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms, for example, freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se. Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. Nos. 2,868,691 or 3,095, 355 may be used.

Best Mode for Carrying Out the Invention

The following reference examples and examples illustrate the present invention, but do not limit the present invention.

The solvents in the parenthesis show the eluting or developing solvents and the ratios of the solvents used are by volume in chromatographic separations or TLC.

The solvents in the parentheses in NMR show the solvents used in measurement.

In the structure, Boc is t-butoxycarbonyl.

REFERENCE EXAMPLE 1

4(2-nitrophenyl)butanoic acid methyl ester

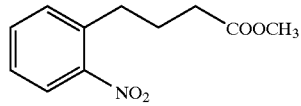

To a suspension of zinc powder (851 mg) in tetrahydrofuran (THF; 4 ml), a catalytic amount of chloromethylsilane under reflux. A solution of 4-iodebutanoicacid methyl ester (1.98 g) in THF (5 ml) was dropped slowly into this suspension and refluxed 3 hours. The mixture was cooled by allowing to stand and so a solution of 3-carbomethoxypropyl-zinc (II) iodide (alkyl zinc) in THP was prepared.

After deaeration, bis(dibenzylideneacetone)palladium (333 mg), 1,1'-bis(dipheylphosphino)ferrocene (321 mg) and the above prepared solution of alkyl zinc in THF were added to a solution of 1-iode-2-nitrobenzene (1.442 g) in THF (6 ml), and the mixture was stirred for 1.5 hours at 50° C. The reaction mixture was cooled. A saturated aqueous solution of ammonium chloride was added to the mixture. The mixture was extracted with ethyl acetate. The organic layer was washed with water and a saturated aqueous solution of sodium chloride, dried over magnesium sulfate and concentrated. The residue was purified by column chromatography on silica gel to give the title compound (784 mg) having the following physical data.

TLC: Rf 0.47 (n-hexane:ethyl acetate=4:1);

NMR(200 MHz, CDCl$_3$): δ7.91 (m, 1H), 7.53 (m, 1H), 7.42–7.31 (m, 2H), 3.69 (s, 3H), 2.93 (t, J=7.6 Hz, 2H), 2.41 (t, J=7.4 Hz, 2H), 2.01 (m, 2H).

REFERENCE EXAMPLE 2

4-(2-aminophenyl)butanoic acid methyl ester

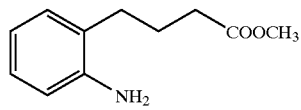

Under an atmosphere of argon, 10% palladium carbon (80 mg; 10 w %) was added to a solution of the compound prepared in reference example 1 (780 mg) in methanol (5 ml). The mixture was stirred for 3 hours at room temperature under atmosphere of hydrogen gas. The reaction mixture was filtered through celite (trademark). The filtrate was concentrated. The residue was purified by column chromatography on silica gel to give the title compound (567 mg) having the following physical data.

TLC: Rf 0.36 (n-hexane:ethyl acetate=3:1);

NMR(200 MHz, CDCl$_3$): δ7.07–6.98 (m, 2H), 6.74–6.65 (m, 2H), 3.80 (br, 2H), 3.69 (s, 3H), 2.53 (m, 2H), 2.41 (t, J=6.9 Hz, 2H), 1.92 (m, 2H).

EXAMPLE 1

4-[2-[2-(1-naphthyl)propanoylamino]phenyl]butanoic acid methyl ester

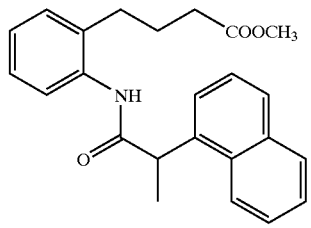

To a solution of the compound prepared in reference example 2 (300 mg) and pyridine (0.25 ml) in methylene chloride (1 ml), a solution of 2-(1-naphthyl)propionyl chloride (389 mg) in methylene chloride (2 ml) was added under cooling with ice. The mixture was stirred for 3 hours at room temperature. To the reaction mixture, a saturated aqueous solution of sodium bicarbonate was added. The mixture was extracted with ethyl acetate, The organic layer was washed with water and a saturated aqueous solution of sodium chloride, dried over magnesium sulfate and concentrated. The crude crystals was recrystallized with ethyl acetate/hexane to give the title compound (441 mg) having the following physical data.

TLC Rf 0.40 (toluene:ethyl acetate=9:1);

NMR(200 MHz, CDCl$_3$): δ8.20 (m, 1H), 7.98–7.80 (m, 3H), 7.66 (m, 1H), 7.60–7.46 (m, 3H), 7.38 (brs, 1H), 7.18 (m, 1H), 7.02–6.97 (m, 2H), 4.65 (q, J=7.0 Hz, 1H), 3.58 (s, 3H), 2.06–1.90 (m, 4H), 1.82 (d, J=7.0 Hz, 3H), 1.32 (m, 2H).

EXAMPLE 1(1)–1(2)

The following compounds were obtained by the same procedure as a series of reactions of Reference example 1→Reference example 2→Example 1, using corresponding compounds.

EXAMPLE 1(1)

4-[4-cyano-2-[2-(1-naphthyl)propanoylamino]phenyl]bitanoic acid methyl ester

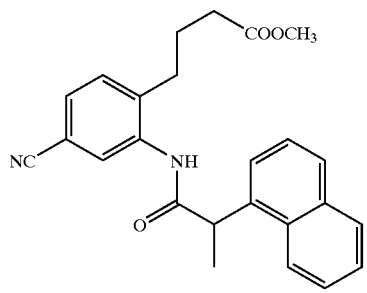

TLC: Rf 0.40 (n-hexane:ethyl acetate 2:1);

NMR(300 MHz, CDCl$_3$): δ8.50 (d, J=1.5 Hz, 1H), 8.18 (m, 1H), 7.90 (m, 1H), 7.84 (d, J=8.1 Hz, 1H), 7.81 (br, 1H), 7.64 (m, 1H), 7.58 7.48 (m, 3H), 7.27 (dd, J=7.8, 1.5 Hz, 1H), 7.09 (d, J=7.8 Hz, 1H), 4.72 (q, J=7.2 Hz, 1H), 3.57 (s, 3H), 2.11 (m, 2H), 2.03 (m, 2H), 1.80 (d, J=7.2 Hz, 3H), 1.38 (m, 2H).

EXAMPLE 1(2)

4-[4-cyano-2-[2-(1-naphthyl)propanoylamino] phenyl]butanoic acid butyl ester

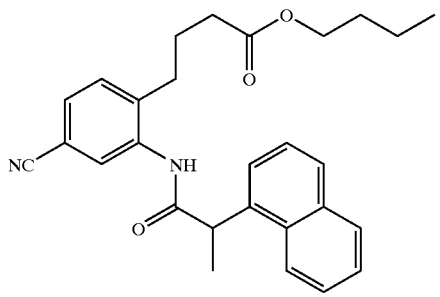

TLC: Rf 0.49 (n-hexane:ethyl acetate=3:1);

NMR(300 MHz, CDCl$_3$): δ8.51 (d, J=1.8 Hz, 1H;), 8.18 (m, 1H), 7.96 7.80 (m, 3H), 7.64 (dd, J=7.2, 0.9 Hz, 1H), 7.57–7.47 (m, 3H), 7.27 (dd, J=7.8, 1.8 Hz, 1H), 7.09 (d, J=7.8 Hz, 1H), 4.74 (q, J=7.2 Hz, 1H), 4.00 (m, 1H), 3.88 (m, 1H), 2.15 (m, 2H), 2.05 (m, 2H), 1.79 (d, J=7.2 Hz, 3H), 1.55 (m, 2H), 1.35 (m, 4H), 0.94 (t, J=7.5 Hz, 3H).

EXAMPLE 2

4-[2-[2-(1-naphthyl)propanoylamino]phenyl]butanoic acid

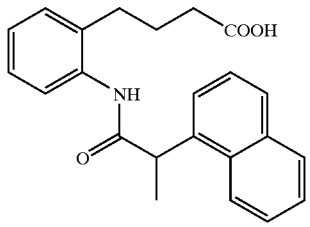

To a solution of the compound prepared in Example 1 (436 mg) in methanol/dioxane (1:2; 6 ml), 2M aqueous solution of sodium hydroxide (3 ml) was added, and the mixture was stirred for 2 hours at 50° C. The reaction mixture was acidified by adding hydrochloric acid, and the mixture was extracted with ethyl acetate. The organic layer was washed with water and a saturated aqueous solution of sodium chloride, dried over magnesium sulfate and concentrated. The crude crystal was washed with ethyl acetate to give the title compound (288 mg) having the following physical data.

TLC: Rf 0.36 (n-hexane:ethyl acetate=1:2);

NMR(300 MHz, d$_6$-DMSO): δ12.04 (brs, 1H), 9.46 (brs, 1H), 8.31 (d, J=8.4 Hz, 1H), 7.94 (m, 1H), 7.83 (d, J=8.4 Hz, 1H), 7.62–7.47 (m, 4H), 7.27 (m, 1H), 7.19–7.07 (m, 3H), 4.69 (q, J=6.9 Hz, 1H), 2.43 (m, 2H), 2.02 (t, J=7.2 Hz, 2H), 1.59 (d, J=6.9 Hz, 3H), 1.56 (m, 2H).

EXAMPLE 2(1)–2(24)

The following compounds were obtained by the same procedure as a series of reactions of Reference example 1→Reference example 2→Example 1→Example 2, using corresponding compounds.

EXAMPLE 2(1)

4-[2-[2-(4-pentylphenyl)propanoylamino]phenyl] butanoic acid

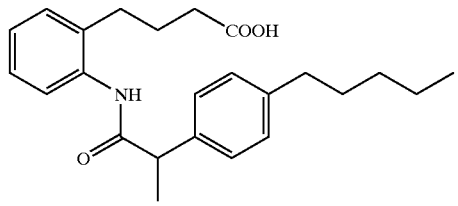

TLC: Rf 0.54 (chloroform:methanol=10:1);

NMR(200 MHz, CDCl$_3$): δ7.93 (d, J=8.0 Hz, 1H), 7.40–6.96 (m, 8H), 3.80 (q, J=7.4 Hz, 1H), 2.59 (t, J=7.8 Hz, 2H), 2.42–2.20 (m, 2H), 2.24 (t, J=6.8 Hz, 2H), 1.74–1.48 (m, 7H), 1.44–1.18 (m, 4H), 0.89 (t, J=6.6 Hz, 3H).

EXAMPLE 2(2)

4-[2-[2-[4-(2-phenylethoxy)phenyl]propanoylamino] phenyl]butanoic acid

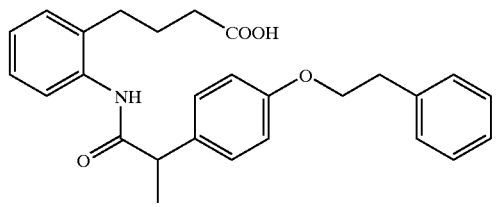

TLC: Rf 0.28 (n-hexane:ethyl acetate=1:1);

NMR(300 MHz, CDCl$_3$): δ7.93 (d, J=8.4 Hz, 1H), 7.40–7.15 (m, 9H), 7.10–7.00 (m, 2H), 6.95–6.85 (m, 2H), 4.16 (t, J=7.1 Hz, 2H), 3.77 (q, J=7.1 Hz, 1H), 3.09 (t, J=7.1 Hz, 2H), 2.33 (m, 2H), 2.25 (t, J=7.1 Hz, 2H), 1.62 (m, 2H), 1.58 (d, J=7.1 Hz, 3H).

EXAMPLE 2(3)

4-[4-cyano-2-[3-cyclopropyl-2-(1-naphthyl) propanoylamino]phenyl]butanoic acid

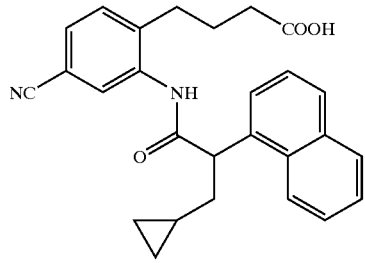

TLC: Rf 0.49 (chloroform:methanol=10:1);

NMR(300 MHz, CDCl$_3$): δ8.41 (s, 1H), 8.21 (d, J=7.5 Hz, 1H), 7.91 (m, 1H), 7.84 (d, J=7.5 Hz, 1H), 7.69–7.46 (m,

5H), 7.28 (m, 1H), 7.09 (d, J=7.5 Hz, 1H), 4.61 (t, J=7.2 Hz, 1H), 2.32–1.96 (m, 6H), 1.36 (m, 2H), 0.79 (m, 1H), 0.48–0.39 (m, 2H), 0.24–0.08 (m, 2H).

EXAMPLE 2(4)

4-[2-[3-cyclopropyl-2-(1-naphthyl)propanoylamino]phenyl]butanoic acid

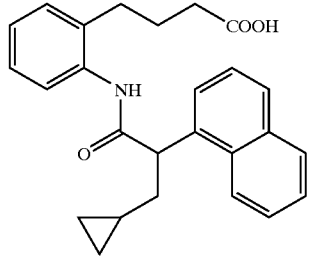

TLC: Rf 0.53 (chloroform:methanol=10:1);

NMR(300 MHz, CDCl): δ8.22 (d, J 8.1 Hz, 1H), 7.93–7.80 (m, 3H), 7.67 (d, J=7.2 Hz, 1H), 7.59–7.47 (m, 3H), 7.18 (m, 1H), 7.00 (d, J 3.3 Hz, 2H), 4.54 (t, J=7.2 Hz, 1H), 2.30–1.92 (m, 6H), 1.33 (m, 2H), 0.79 (m, 1H), 0.48–0.36 (m, 2H), 0.26–0.08 (m, 2H),

EXAMPLE 2(5)

4-[4-cyano-2-[4-methyl-2-(1-naphthyl)pentanoylamino]phenyl]butanoic acid

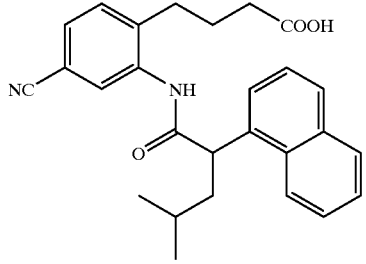

TLC: Rf 0.53 (chloroform:methanol=10:1);

NMR(300 MHz, CDCl$_3$): δ8.42 (s, 1H), 8.21 (d, J=8.1 Hz, 1H), 7.90 (m, 1H), 7.84 (d, J=7.8 Hz, 1H), 7.66–7.48 (m, 5H), 7.28 (m, 1H), 7.09 (d, J=8.1 Hz, 1H), 4.60 (t, J=7.2 Hz, 1H), 2.34 (m, 1H), 2.20–1.88 (m, 5H), 1.70 (m, 1H 1.34 (m, 2H), 1.24 (d, J=6.6 Hz, 3H), 0.98 (d, J=6.6 Hz, 3H).

EXAMPLE 2(6)

4-[4-cyano-2-[2-(1-naphthyl)propanoylamino]phenyl]butanoic acid

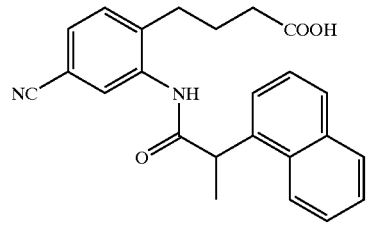

TLC: Rf 0.17 (n-hexane:ethyl acetate=1:1);

NMR(300 MHz, CDCl$_3$): δ8.36 (brs, 1H), 8.11 (brd, J=7.8 Hz, 1H), 7.92 (m, 1H), 7.86 (brd, J=8.4 Hz, 1H), 7.62 (brd, J=6.3 Hz, 1H), 7.60–7.50 (m, 3H), 7.33 (brs, 1H), 7.26 (dd, J=7.8, 1.8 Hz, 1H), 7.07 (d, J=7.8 Hz, 1H), 4.60 (q, J=7.2 Hz, 1H), 2.03–1.87 (m, 4H), 1.82 (d, J=7.2 Hz, 3H), 1.30–1.21 (m, 2H).

EXAMPLE 2(7)

4-[4-fluoro-2-[2-(1-naphthyl)propanoylamino]phenyl]butanoic acid

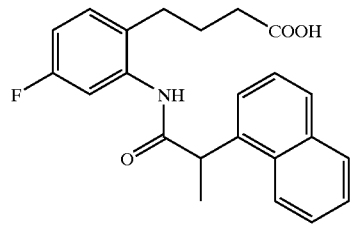

TLC: Rf 0.55 (n-hexane:ethyl acetate=2:1);

NMR(300 MHz, CDCl$_3$): δ 8.12 (d, J=7.5 Hz, 1H), 7.93–7.85 (m, 3H), 7.62 (d, J=6.3 Hz, 1H), 7.59–7.50 (m, 3H), 7.21 (br s, 1H), 6.90 (dd, J=8.4, 6.3 Hz, 1H), 6.68 (dt, J=3.0, 8.4 Hz, 1H), 4.58 (q, J=7.2 Hz, 1H), 1.94–1.82 (m, 7H), 1.23–1.13 (m, 2H).

EXAMPLE 2(8)

4-[4-chloro-2-[2-(1-naphthyl)propanoylamino]phenyl]butanoic acid

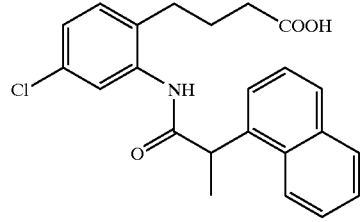

TLC: Rf 0,55 (n-hexane:ethyl acetate=2:1);

NMR(200 MHz, CDCl$_3$): δ8.14–8.04 (m, 2H), 7.94–7.84 (m, 2H), 7.64–7.49 (m, 4H), 7.17 (br s, 1H), 6.97 (dd, J=8.0, 2.0 Hz, 1H), 6.89 (d, J=8.0 Hz, 1H), 4.57 (q, J=7.2 Hz, 1H), 1.95–1.81 (m, 7H), 1.26–1.17 (m, 2H).

EXAMPLE 2(9)

4-[4-methyl-2-[2-(1-naphthyl)propanoylamino]phenyl]butanoic acid

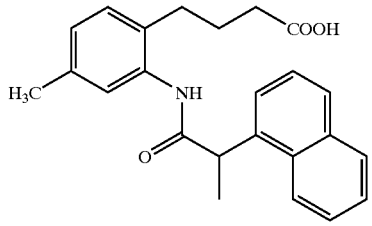

TLC: Rf 0.55 (n-hexane:ethyl acetate=2:1);

NMR(300 MHz, CDCl$_3$): δ8.14 (d, J=7.8 Hz, 1H), 7.92–7.84 (m, 2H), 7.69–7.50 (m, 5H), 7.01 (br s, 1H), 6.87–6.80 (m, 2H), 4.55 (q, J=7.2 Hz, 1H), 2.28 (s, 3H), 1.92–1.83 (m, 7H), 1.26–1.19 (m, 2H).

EXAMPLE 2(10)

4-[4-cyano-2-[2-(4-methyl-1-naphthyl)propanoylamino]phenyl]butanoic acid

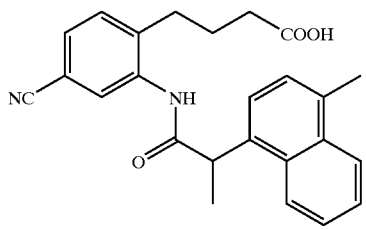

TLC: Rf 0.45 (ethyl acetate),

NMR(300 MHz, CDCl$_3$): δ8.35 (s, 1H), 8.13–8.07 (m, 2H), 7.59–7.56 (m, 2H), 7.50 (d, J=7.5 Hz, 1H), 7.37 (d, J=7.5 Hz, 1H), 7.33 (s, 1H), 7.26 (dd, J=7.8, 1.8 Hz, 1H), 7.06 (d, J=7.5 Hz, 1H), 4.56 (q, J=7.2 Hz, 1H), 2.72 (s, 3H), 1.99–1.90 (m, 4H), 1.81 (d, J=7.2 Hz, 3H), 1.29–1.19 (m, 2H).

EXAMPLE 2(11)

4-[4-cyano-2-[2-(1,2,3,4tetrahydro-5-naphthyl)propanoylamino]phenyl]butanoic acid

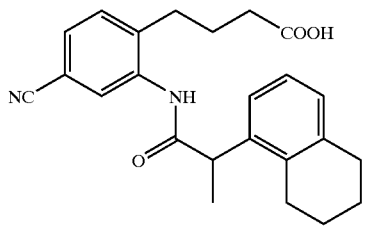

TLC: Rf 0.64 (chloroform:methanol=9:1);

NMR(300 MHz, CDCl$_3$): δ 8.43 (brs, 1H), 7.35–7.02 (m, 6H), 4.04 (q, J=6.9 Hz, 1H), 2.90–2.60 (m, 4H), 2.29–2.15 (m, 4H), 1.88–1.70 (m, 4H), 1.65 (d, J=6.9 Hz, 3H), 1.56–1.44 (m, 2H).

EXAMPLE 2(12)

4-[4-cyano-2-[2-(4-methoxy-1-naphthyl)propanoylamino]phenyl]butanoic acid

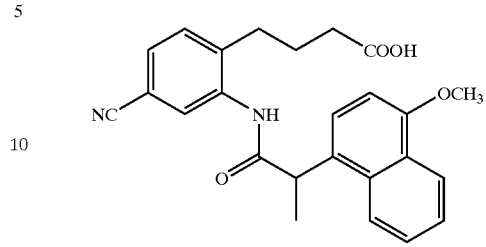

TLC: Rf 0.70 (chloroform:methanol=9:1);

NMR(300 MHz, CDCl$_3$): δ 8.39–8.34 (m, 2H), 8.01 (d, J=7.8 Hz, 1H), 7.60–7.49 (m, 2H), 7.51 (d, J=8.1 Hz, 1H), 7.31 (brs, 1H), 7.25 (dd, J=8.1, 1.5 Hz, 1H), 7.05 (4, J=7.8 Hz, 1H), 6.85 (d, J=7.8 Hz, 1H), 4.47 (q, J 7.2 Hz, 1H), 4.03 (s, 3), 1.98–1.84 (m, 4H), 1.80 (d, J=7.2 Hz, 3H), 1.30–1.18 (m, 2H).

EXAMPLE 2(13)

4-[4-ethynyl-2-[2-(1-naphthyl)propanoylamino]phenyl]butanoic acid

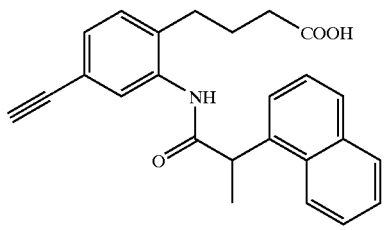

TLC: Rf 0.55 (n-hexane:ethyl acetate=1:2);

NMR(300 MHz, CDCl$_3$): δ8.13 (d, J=8.1 Hz, 1H), 8.05 (s, 1H), 7.93–7.84 (m, 2H), 7.63–7.50 (m, 4H), 7.13 (dd, J=7.8, 1.5 Hz, 1H), 7.09 (s, 1H), 6.93 (d, J=7.5 Hz, 1H), 4.57 (q, J=7.2 Hz, 1H), 3.01 (s, 1H), 1.94–1.89 (m, 4H), 1.83 (d, J=7.2 Hz, 3H), 1.29–1.19 (m, 2H).

EXAMPLE 2(14)

4-[4-cyano-2-[2-(benzothiophen-3-yl)propanoylamino]phenyl]butanoic acid

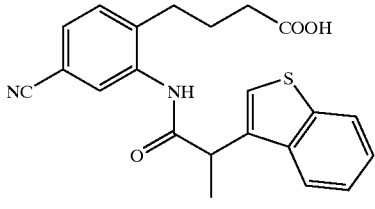

TLC: Rf 0.29 (n-hexane:ethyl acetate=1:2);

NMR(300 MHz, d$_6$-DMSO): δ12.10 (s, 1H), 9.74 (s, 1H), 8.01–7.95 (m, 2H), 7.83 (d, J=1.8 Hz, 1H), 7.63 (s, 1H), 7.58 (dd, J=7.8, 1.8 Hz, 1H), 7.46–7.34 (m, 3H), 4.35 (q, J=6.9 Hz, 1H), 2.59 (m, 2H), 2.08 (t, J=7.2 Hz, 2H), 1.60 (m, 2H), 1.59 (d, J=6.9 Hz, 3H).

EXAMPLE 2(15)

4-[4-cyano-2-[2-(4-fluoro-1-naphthyl)propanoylamino]phenyl]butanoic acid

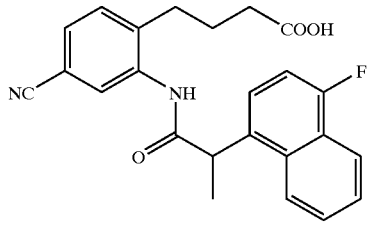

TLC: Rf 0.41 (chloroform:methanol=30:1);

NMR(300 MHz, CDCl$_3$): δ8.37 (brs, 1H), 8.20 (m, 1H), 8.12 (m, 1H); 7.66–7.50 (m, 4H), 7.28 (dd, J 8.1, 1.8 Hz, 1H), 7.19 (dd, J=9.9, 8.1 Hz, 1H), 7.10 (d, J=7.2 Hz, 1H), 4.57 (q, J=7.2 Hz, 1H), 2.20–2.00 (m, 4H), 1.79 (d, J=7.2 Hz, 3H), 1.43–1.30 (m, 2H).

EXAMPLE 2(16)

4-[4-cyano-2-[2(R)-(1-naphthyl)propanoylamino]phenyl]butanoic acid

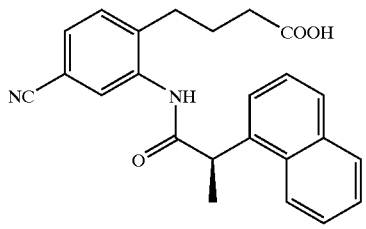

TLC: Rf 0.65 (ethyl acetate);

NMR(300 MHz, CDCl$_3$): δ8.37 (s, 1H), 8.12 (d, J=8.4 Hz, 1H), 7.94–7.85 (m, 2H), 7.63–7.50 (m, 4H), 7.36 (s, 1H), 7.27 (dd, J=7.8, 1.8 Hz, 1H), 7.07 (d, J=8.1 Hz, 1H), 4.60 (q, J=7.2 Hz, 1H), 2.04–1.92 (m, 4H), 1.82 (d, J=7.2 Hz, 3H), 1.31–1.21 (m, 2H).

EXAMPLE 2(17)

4-[5-cyano-2-[2-(1-naphthyl)propanoylamino]phenyl]butanoic acid

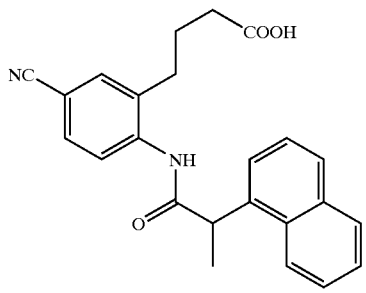

TLC: Rf 0.45 (n-hexane:ethyl acetate=1:2);

NMR(300 MHz, DMSO): δ12.11 (s, 1H), 9.67 (s, 1H), 8.26 (d, J=8.7 Hz, 1H), 7.95 (dd, J=7.2, 1.5 Hz, 1H), 7.84 (d, J=7.2 Hz, 1H), 7.70–7.47 (m, 7H), 4.77 (q, J=6.9 Hz, 1H), 2.56–2.54 (m, 2H), 2.07 (t, J=7.2 Hz, 2H), 1.61–1.53 (m, 5H).

EXAMPLE 2(18)

5-[4-cyano-2-[2-(1-naphthyl)propanoylamino]phenyl]pentanoic acid

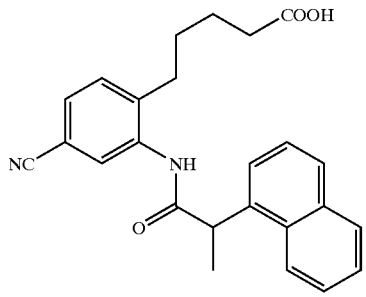

TLC: Rf 0.65 (ethyl acetate);

NMR(300 MHz, d$_6$-DMSO): δ11.95 (br s, 1H), 9.64 (s, 1H), 8.28 (d, J=8.1 Hz, 1H), 7.94 (d, J=7.5 Hz, 1H), 7.85–7.80 (m, 2H), 7.62–7.48.(m, 5H), 7.37 (d, J=8.1 Hz, 1H), 4.72 (q, J=6.9 Hz, 1H), 2.04–2.00 (m, 2H), 1.60 (d, J=6.9 Hz, 3H), 1.27 (m, 4H).

EXAMPLE 2(19)

3-[4-cyano-2-[2-(1-naphthyl)propanoylamino]phenyl]propionic acid

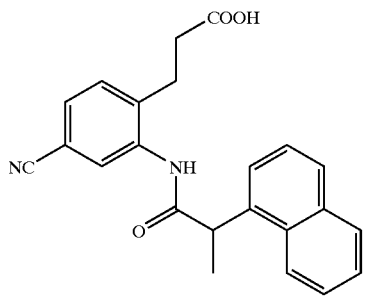

TLC: Rf 0.45 (ethyl acetate);

NMR (300 MHz, d$_6$-DMSO): δ12.21 (br s, 1H), 9.82 (s, 1H), 8.26 (d, J=8.7 Hz, 1H), 7.95 (d, J=7.8 Hz, 1H), 7.85–7.78 (m, 2H), 7.60–7.41 (m, 6H), 4.73 (q, J=6.9 Hz, 1H), 2.80 (t, J=7.5 Hz, 2H), 2.41 (t, J=7.5 Hz, 2H), 1.60 (d, J=6.9 Hz, 3H).

EXAMPLE 2(20)

3-[4-cyano-2-[4-methyl-2-(1-naphthyl)pentanoylamino]phenyl]propionic acid

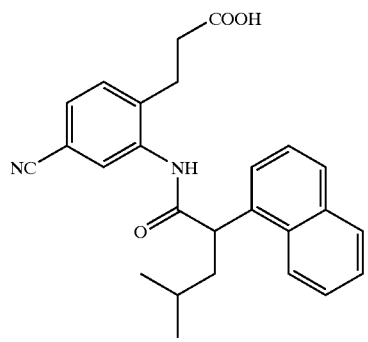

TLC: Rf 0.44 (chloroform:methanol=10:1);

NMR(300 MHz, CDCl$_3$): δ8.22–8.05 (m, 3H), 7.88 (m, 1H), 7.80 (d, J=8.4 Hz, 1H), 7.66–7.44 (m, 4H), 7.29 (dd, J=7.8, 1.5 Hz, 1H), 7.11 (d, J=8.1 Hz, 1H), 4.49 (t, J=7.2 Hz, 1H), 2.40–2.16 (m, 5H), 2.00 (m, 1H), 1.69 (m, 1H), 1.02 (t, J=6.6 Hz, 3H), 0.98 (t, J=6.6 Hz, 3H).

EXAMPLE 2(21)

4-[4-cyano-2-[2-(1,4-benzodioxan-5-yl)propanoylamino]phenyl]butanoic acid

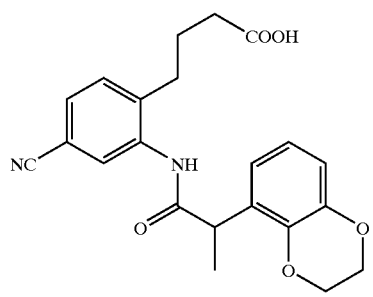

TLC: Rf 0.59 (chloroform:methanol 9:1);

NMR(300 MHz, CDCl$_3$): δ8.38 (brs, 1H), 7.52 (brs, 1H), 7.33 (dd, J=7.8, 1.5 Hz, 1H), 7.18 (d, J=7.8 Hz, 1H), 6.97–6.83 (m, 3H), 4.40–4.25 (m, 4H), 4.13 (q, J=7.2 Hz, 1H), 2.45–2.37 (m, 2H), 2.34–2.20 (m, 2H), 1.72–1.61 (m, 2H), 1.58 (d, J=7.2 Hz, 3H).

EXAMPLE 2(22)

4-[4-cyano-2-[2-(2-methyl-1-naphthyl)propanoylamino]phenyl]butanoic acid

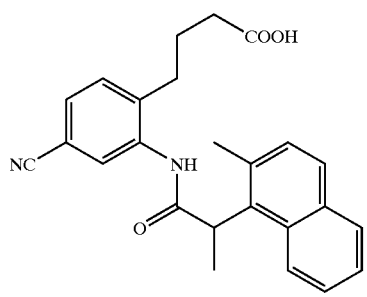

TLC: Rf 0.60 (ethyl acetate);

NMR(300 MHz, CDCl$_3$): δ8.32 (s, 1H), 7.92–7.85 (m, 2H), 7.79 (d, J=8.4 Hz, 1H), 7.51–7.39 (m, 3H), 7.26 (dd, J=7.8, 1.5 Hz, 1H), 7.05 (d, J=7.8 Hz, 1H), 6.98 (s, 1H), 4.59–4.57 (m, 1H), 2.62 (s, 3H), 1.89–1.70 (m, 7H), 1.22–1.05 (m, 2H).

EXAMPLE 2(23)

4-[4-cyano-2-[2-(2-methoxy-1-naphthyl)propanoylamino]phenyl]butanoic acid

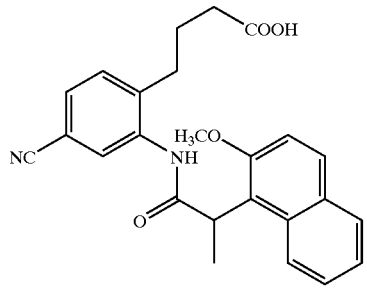

TLC: Rf 0.70 (chloroform:methanol=9:1);

NMR(300 MHz, CDCl$_3$): δ8.36 (brs, 1H), 7.95 (d, J=8.7 Hz, 1H), 7.90–7.83 (m, 2H), 7.51 (m, 1H), 7.41–7.34 (m, 2H), 7.25 (dd, J=8.1, 1.5 Hz, 1H), 7.13 (brs, 1H), 7.07 (d, J=8.1 Hz, 1H), 4.84 (q, J=7.2 Hz, 1H), 3.99 (s, 3H), 2.02–1.80 (m, 4H), 1.70 (d, J=7.2 Hz, 3H), 1.39–1.20 (m, 2H).

EXAMPLE 2(24)

4-[4cyano-2-[2-(indol-3-yl)propanoylamino]phenyl]butanoic acid

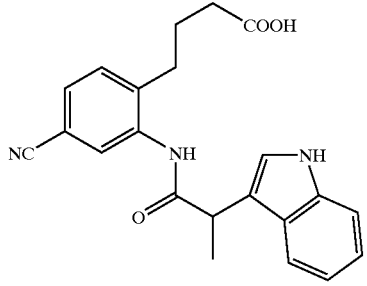

TLC: Rf 0.55 (ethyl acetate);

NMR(300 MHz, CDCl$_3$): δ8.44 (m, 2H), 7.70–7.64 (m, 2H), 7.42 (d, J=8.1 Hz, 1H), 7.28–7.22 (m, 3H), 7.18–7.12 (m, 1H), 7.08 (d, J=7.8 Hz, 1H), 4.14 (q, J=7.2 Hz, 1H), 2.06–1.95 (m, 4H), 1.76 (d, J=7.2 Hz, 3H), 1.39–1.30 (m, 2H).

EXAMPLE 3

4-[4-cyano-2-[2-(1-naphthyl)propanoylamino]phenyl]butanol

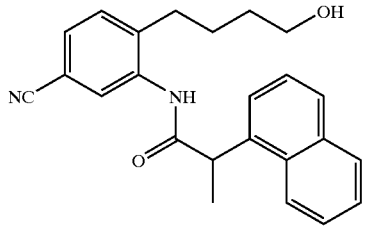

Under an atmosphere of argon, to a solution of the compound prepared in Example 2(6) (169 mg) in THF (1 ml), a solution of borane-THF complex (0.47 ml) was added at 0° C. The mixture was stirred for 5 hours at room temperature. Water was added to the reaction mixture, and the mixture was extracted with ethyl acetate. The organic layer was washed with water and a saturated aqueous solution of sodium chloride, dried over anhydrous magnesium sulfate and concentrated. The residue was purified by column chromatography on silica gel to give the title compound (65 mg) having the following physical data.

TLC: Rf 0.35 (n-hexane:ethyl acetate=1:2);

NMR(300 MHz, CDCl$_3$): δ8.38 (s, 1H), 8.10–8.07 (m, 1H), 7.95–7.88 (m, 2H), 7.63–7.53 (m, 4H), 7.27–7.23 (m, 1H), 7.13 (s, 1H), 7.05 (d, J=8.1 Hz, 1H), 4.54 (q, J=7.2 Hz, 1H), 3.35–3.25 (m, 2H), 1.90–1.85 (m, 2H),1.84 (d, J=7.2 Hz, 3H), 1.06–0.90 (m, 4H),

EXAMPLE 4

N-[4-[2-[2-(1-naphthyl)propanoylamino]phenyl]butanoyl]-(3,5-dimethylisoxazol-4-yl)sulfonamide

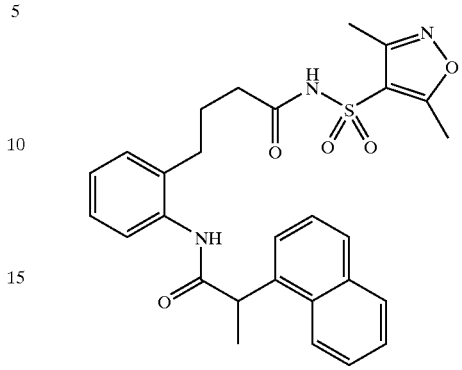

To a solution of the compound prepared in Example 2 (150 mg) in methylene chloride (2 ml), (3,5-dimethylisoxazol-4-yl)sulfonamide (147 mg), 1-ethyl-3-[3-(dimethylamino)propyl]carbodiimide (120 mg) and 4-dimethylaminopyridine (15 mg) were added. The mixture was stirred overnight at room temperature. 1M hydrochloric acid was added to the reaction mixture, and the mixture was extracted with ethyl acetate. The organic layer was washed with water and a saturated aqueous solution of sodium chloride, dried over anhydrous magnesium sulfate and concentrated. The residue was purified by column chromatography on silica gel, and washed with a mixture of methanol and water to give the title compound (121 mg) having the following physical data.

TLC: Rf 0.53 (n-hexane:ethyl acetate=2:3);

NMR(300 MHz, d$_6$-DMSO): δ12.3 (brs, 1H), 9.42 (brs, 1H), 8.28 (d, J=8.4 Hz, 1H), 7.93 (m, 1H), 7.82 (d, J=8.1 Hz, 1H), 7.60–7.45 (m, 4H), 7.25 (m, 1H), 7.18–7.06 (m, 3H), 4.66 (q, J 6.9 Hz, 1H), 2.64 (s, 3H), 2.40–2.30 (m, 2H), 2.36 (s, 3H), 2.11 (t, J=7.5 Hz, 2H), 1.58 (d, J=6.9 Hz, 3H), 1.51 (m, 2H).

EXAMPLE 4(1)-4(2)

The following compounds were obtained by the same procedure as a reaction of Example 4, using the compound prepared in Example 2(6) and a corresponding compound.

EXAMPLE 4(1)

N-[4-[4-cyano-2-[2-(1-naphthyl)propanoylamino]phenyl]butanoyl]benzenesulfonamide

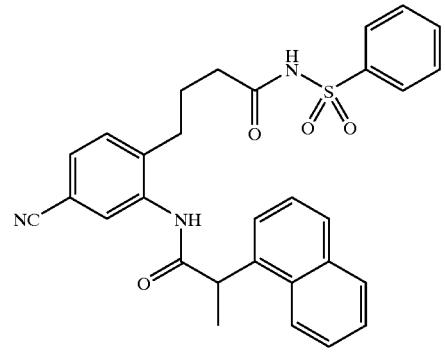

TLC: Rf 0.53 (n-hexane:ethyl acetate=1:3);

NMR(300 MHz, d$_6$-DMSO): δ12.05 (s, 1H), 9.60 (s, 1H), 8.22 (d, J 8.4 Hz, 1H), 7.95 7.88 (m, 3H), 7.82 7.75 (m, 2H), 7.70 (m, 1H), 7.65 7.41 (m, 7H), 7.24 (d, J=8.4 Hz, 1H), 4.68 (q, J=6.9 Hz, 1H), 2.40 (m, 2H), 2.06 (t, J=7.2 Hz, 2H), 1.56 (d, J=6.9 Hz, 3H), 1.45 (m, 2H).

EXAMPLE 4(2)

N-[4-[4-cyano-2-[2-(1-naphthyl)propanoylamino]phenyl]butanoyl]methanesulfonamide

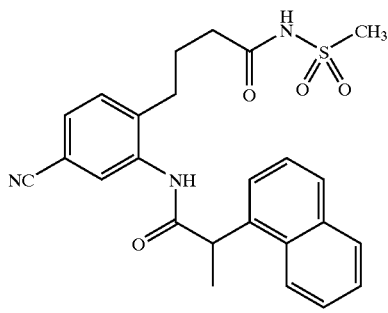

TLC: Rf 0.33 (n-hexane:ethyl acetate=1:3);

NMR(300 MHz, d$_6$-DMSO) δ11.65 (br, 1H), 9.68 (s, 1H), 8.27 (d, J=8.1 Hz, 1H), 7.95 (m, 1H), 7.84 (d, J=8.1 Hz, 1H), 7.82 (d, J=1.5 Hz, 1H), 7.6–7.47 (m, 5H), 7.38 (d, J=8.1 Hz, 1H), 4.74 (q, J=6.9 Hz, 1H), 3.21 (s, 3H) 2.55 (m, 2H), 2.15 (t, J=7.2 Hz, 2H), 1.60 (m, 2H), 1.60 (d, J=6.9 Hz, 3H).

REFERENCE EXAMPLE 3

(2-nitrobenzyl)thioacetic acid

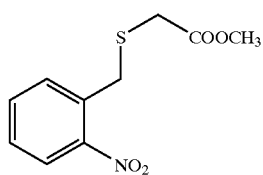

A solution of o-nitrobenzyl bromide (2.68 g) and potassium thioacetate (1.42 g) in acetone (20 ml) was refluxed for 2 hours. Water was added to the reaction mixture, and the mixture was extracted with ethyl acetate. The organic layer was washed with water and a saturated aqueous solution of sodium chloride, dried over anhydrous magnesium sulfate and concentrated, and then (2-nitrobenzyl)thioacetate was obtained.

To a solution of the obtained compound and methyl bromoacetate (1.4 ml) in methanol (15 ml), sodium methoxide (737 mg) was added, and the mixture was stirred for 1 hour at 45° C. Potassium t-butoxide (1.39 g) was added to the reaction mixture, and the mixture was stirred for 30 minutes. Water was added to the reaction mixture, and the mixture was extracted with ethyl acetate. The organic layer was washed with water and a saturated aqueous solution of sodium chloride, dried over magnesium sulfate and concentrated. The residue was purified by column chromatography on silica gel to give the title compound (2.55 mg) having the following physical data.

TLC: Rf 0.26 (n-hexane:ethyl acetate=4:1);

NMR(200 MHz, CDCl$_3$): δ8.02 (dd, J=8.0, 1.0 Hz, 1H), 7.63–7.40 (m, 3H), 4.21 (s, 2H), 3.72 (s, 3H), 3.09 (s, 2H).

EXAMPLE 5

2-[2-(1-naphthyl)propanoylamino]benzylthioacetic acid

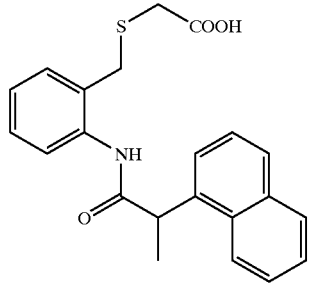

The title compound having the following physical data was obtained by the same procedure as a series of reactions of Reference example 2→Example 1→Example 2, using the compound prepared in Reference example 3.

TLC: Rf 0.34 (chloroform:methanol:water=90:10:1);

NMR(200 MHz, CDCl$_3$): δ8.12 (m, 1H), 7.96–7.78 (m, 3H), 7.72 (brs, 1H), 7.66–7.46 (m, 4H), 7.26 (m, 1H), 7.04–6.96 (m, 2H), 4.53 (q, J=7.2 Hz, 1H), 3.10 (d, J=13.6 Hz, 1H), 2.98 (d, J=13.6 Hz, 1H), 2.60 (s, 2H), 1.86 (d, J=7.2 Hz, 3H).

EXAMPLE 5(1)

4-cyano-2-[2-(1-naphthyl)propanoylamino]benzylthioacetic acid

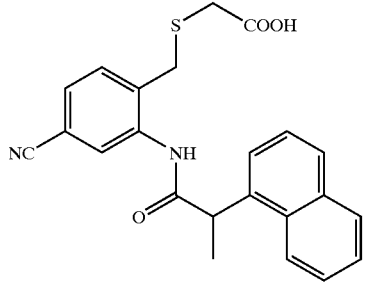

The title compound having the following physical data was obtained by the same procedure as a series of reactions of Reference example 3→Example 5, using a corresponding compound.

TLC: Rf 0.20 (ethyl acetate:methanol=9:1);

NMR(300 MHz, d$_6$-DMSO): δ9.74 (s, 1H), 8.25 (d, J=7.8 Hz, 1H), 7.97–7.94 (m, 2H), 7.85 (d, J=7.8 Hz, 1H), 7.62–7.45 (m, 6H), 4.77 (q, J=6.9 Hz, 1H), 3.90–3.79 (m, 2H), 3.05 (s, 2H), 1.61 (d, J=6.9 Hz, 3H).

REFERENCE EXAMPLE 4

N-(5-cyano-2-methoxymethoxyphenyl)-4methyl-2-(1-naphthyl)pentanamide

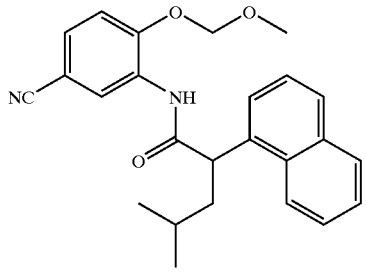

To a solution of 4-methyl-2-(1-naphthyl)valeryl chloride (490 mg) in toluene (4 ml), oxalyl chloride (190 μl) and dimethylformamide (DMF; one drop) were added at room temperature. The mixture was stirred for 30 minutes at 50° C. The reaction mixture was concentrated, and the residue was dissolved into methylene chloride. The solution was dropped into a solution of 2-amino-4-cyano-1-methoxymethoxybenzene (480 mg) in methylene chloride (5 ml), and then the mixture was stirred for 30 minutes. 2N hydrochloric acid was added to the reaction mixture, and the mixture was extracted with chloroform. The organic layer was washed with a saturated aqueous solution of sodium chloride, dried over magnesium sulfate and concentrated The residue was purified by column chromatography on silica gel (n-hexane:ethyl acetate=4:1) to give the title compound (684 mg) having the following physical data.

TLC: Rf 0.55 (n-hexane:ethyl acetate=2:1);

NMR(200 MHz, CDCl$_3$) δ8.71 (d, J=2.2 Hz, 1H), 8.20–8.08 (m, 1H), 7.96–7.68 (m, 3H), 7.66–7.42 (m, 4H), 7.22 (dd, J=8.4, 1.8 Hz, 1H), 6.92 (d, J=8.4 Hz, 1H), 4.82 (s, 2H), 4.48 (t, J=7.5 Hz, 1H), 2.98 (s, 3H), 2.44–2.25 (m, 1H), 2.12–1.94 (m, 1H), 1.80 (m, 1H), 1.00 (d, J 6.8 Hz, 3H), 0.97 (d, J 6.8 Hz, 3H).

REFERENCE EXAMPLE 5

N-(5-cyano-2-hydroxyphenyl)-4-methyl-2-(1-naphthyl)pentanamide

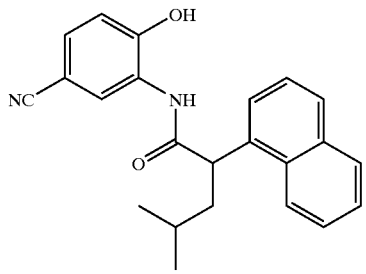

To a solution of the compound prepared in Reference example 4 (684 mg) in dioxane (3 ml), 4N hydrochloric acid/dioxane (2.2 ml) was added at 0° C. The mixture was stirred for 5 hours at room temperature. The reaction mixture was concentrated and distilled off an azeotropic mixture with toluene to give the title compound (593 mg) having the following physical data.

TLC: Rf 0.25 (n-hexane:ethyl acetate=2:1);

NMR (200 MHz, d$_6$-DMSO): δ11.13 (brs, 1H), 9.61 (s, 1H), 8.48–8.34 (m, 2H), 8.00–7.78 (m, 2H), 7.70–7.32 (m, 5H), 6.95 (d, J=8.4 Hz, 1H), 5.02–4.88 (m, 1H), 2.20–1.96 (m, 1H), 1.74–1.46 (m, 2H), 1.03 (d, J=6.0 Hz, 3H), 0.91 (d, J=6.0 Hz, 3H).

EXAMPLE 6

4-cyano-2-[4methyl-2-(1-naphthyl)pentanoylamino]phenyloxyacetic acid ethyl ester

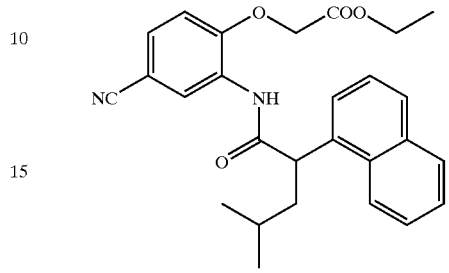

To a solution of the compound prepared in Reference example 5 (290 mg) in acetone (4 ml), potassium carbonate (340 mg), ethyl bromoacetate (0.14 ml) and sodium iodide (12 mg) were added. The mixture was stirred for 2 hours at 50° C. The reaction mixture was cooled to room temperature, and filtered. The filtrate was poured into water, and the mixture was extracted with ether. The organic layer was a saturated aqueous solution of sodium chloride, dried over magnesium sulfate and concentrated. The residue was putrified by column chromatography on silica gel (n-hexan:ethyl acetate=1:1) to give the title compound (349 mg) having the following physical data.

TLC: Rf 0.67 (n-hexane:ethyl acetate=1:1);

NMR(300 MHz, CDCl$_3$): δ8.76 (d, J=2.1 Hz, 1H), 8.24–8.06 (m, 2H), 7.91–7.77 (m, 2H), 7.67–7.46 (m, 4H), 7.27–7.21 (m, 1H), 6.70 (d, J=8.1 Hz, 1H), 4.52 (t, J=7.8 Hz, 1H), 4.17 (q, J=7.2 Hz, 2H), 2.38–2.26 (m, 1H) 2.02–1.90 (m, 1H), 1.76–1.60 (m, 1H), 1.23 (t, J=7.2 Hz, 3H), 1.02 (d, J=6.6 Hz, 3H), 0.97 (t, J=6.6 Hz, 3H).

EXAMPLE 7

4-cyano-2-[4-methyl-2-(1-naphthyl)pentanoylamino]phenyloxyacetic acid

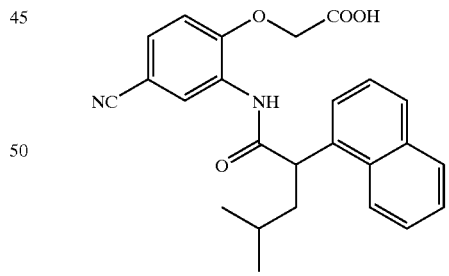

The title compound (159 mg) having the following physical data was obtained by the same procedure as a reaction of Example 2, using the compound prepared in Example 6 (349 mg).

TLC: Rf 0.19 (chloroform:methanol=5:1);

NMR(200 MHz, CDCl$_3$): δ8.66 brs, 1H), 8.16 (d, J=8.0 Hz, 1H), 8.00 (s, 1H), 7.94–7.72 (m, 2H), 7.68–7.38 (m, 4H), 7.30–7.16 (m, 1H), 6.69 (d, J=8.8 Hz, 1H), 4.60–4.40 (m, 1H), 4.47 (s, 2H), 2.40–2.18 (m, 1H), 2.10–1.86 (m, 1H), 1.78–1.50 (m, 1H), 0.99 (d, J=7.0 Hz, 3H), 0.95 (d, J=7.0 Hz, 3H).

EXAMPLE 7(1)

4-cyano-2-[2-(1-naphthyl)propanoylamino]benzyloxyacetic acid

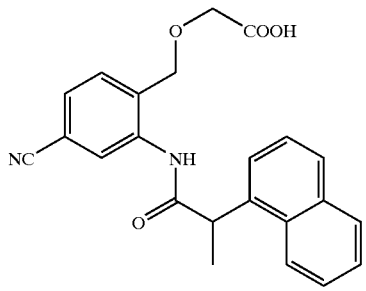

The title compound having the following physical data was obtained by the same procedure as a reaction of Reference example 4→Reference example 5→Example 6→Example 7, using a corresponding compound.

TLC: Rf 0.10 (ethyl acetate:methanol=9:1);

NMR(300 MHz, CDCl$_3$): δ8.61 (s, 2H), 8.11–8.08 (m, 1H), 7.92–7.89 (m, 1H), 7.83 (d, J=8.1 Hz, 1H), 7.59–7.47 (m, 4H), 7.30–7.27 (m, 1H), 7.14 (d, J=8.1 Hz, 1H), 4.60 (q, J=7.2 Hz, 1H), 4.18 (d, J=11.1 Hz, 1H), 4.06 (d, J=11.1 Hz, 1H), 3.55 (d, J=17.1 Hz, 1H), 3.48 (d, J=17.1 Hz, 1H), 1.78 (d, J=7.2 Hz, 3H).

REFERENCE EXAMPLE 6

4-t-butoxycarbonylamino-3-(4-methoxymethyloxy-2-butenyl)pyridine

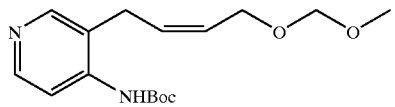

To a solution of t-butyldicarbonate (9.59 g) in THF (40 ml), 4-aminopyridine (3.76 g) was added. The mixture was stirred for 1 hour at room temperature. The solvent was distilled off from the reaction mixture. The obtained solid was washed with hexane/ethyl acetate (1:2), and the solid was obtained by filtration. To a solution of the obtained solid in THF (35 ml), 1.6M n-butyl lithium (9.6 ml) was added at −78° C., and then the mixture was stirred for 2 hours at 0° C. The mixture was cooled −78° C., and a solution of 4-bromo-1-methoxymethoxy-2-butene (1.5 g) in THF (4.0 ml) was dropped into the mixture slowly. The mixture was warmed until 10° C. under stirring for 2 hours. A saturated aqueous solution of ammonium chloride was added to the mixture, and then the mixture was extracted with ethyl acetate. The organic layer was washed with water and a saturated aqueous solution of sodium chloride, dried over magnesium sulfate and concentrated. The residue was purified by column chromatography on silica gel to give the title compound (394 mg) having the following physical data and 4-t-butoxycarbonylaminopyridine.

TLC: Rf 0.13 (n-hexane:ethyl acetate=1:1),

NMR(300 MHz, CDCl$_3$) δ8.37 (d, J=6.0 Hz, 1H), 8.30 (s, 1H), 8.02 (d, J=6.0 Hz, 1), 5.80 (m, 1H), 5.60 (m, 1H), 4.73 (s, 2H), 4.26 (d, J=6.3 Hz, 2H), 3.47 (brd, J=7.5 Hz, 2H), 3.42 (s, 3H).

REFERENCE EXAMPLE 7

N-t-butoxycarbonyl-N-[3-(4methoxymethyloxy-2-butenyl)pyridin-4-yl]-2-naphythylpropanamide

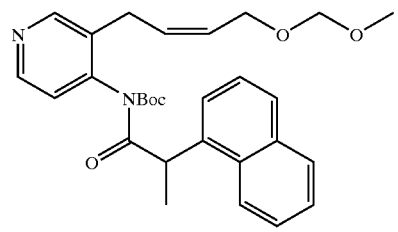

A solution of the compound prepared in Reference example 6 (384 mg) and oxalyl chloride (0.25 ml) in methylene chloride (6.4 ml), DMF (2 μl) was dropped, and the mixture was stirred for 1 hour at room temperature. The reaction mixture was concentrated. The residue was dissolved into dichloroethane (5.0 ml), and then the solution was stirred for 3 hours at 50° C. The reaction mixture was poured into ice water, and extracted with ethyl acetate. The organic layer was washed with 1N hydrochloric acid, water, a saturated aqueous solution of sodium bicarbonate, water and a saturated aqueous solution of sodium chloride, dried over magnesium sulfate and concentrated. The residue was purified by column chromatography on silica gel to give the title compound (290 mg) having the following physical data.

TLC: Rf 0.60 (n-hexane:ethyl acetate=1:1);

NMR(300 MHz, CDCl$_3$): δ8.48–8.43 (m, 10/5H), 8.37 (d, J=6.0 Hz, 3/5H), 8.15 (m, 2/5H), 8.10–8.04 (m, 5/5H), 7.86 (m, 5/5H), 7.76 (m, 5/5H), 7.58–7.37 (m, 20/5H), 6.83 (d, J=5.4 Hz, 2/5H), 6.75 (τd, J=5.4 Hz, 3/5H), 5.80–5.37 (m, 15/5H), 4.67 (s, 6/5H), 4.55 (s, 4/5H), 4.17 (brd, J=7.8 Hz, 6/5H), 3.93 (d, J=7.8 Hz, 4/5H), 3.40 (s, 9/5H), 3.33 (m, 6/5H), 2.93 (brd, J=6.9 Hz, 4/5H), 1.68 (d, J=7.2 HZ, 1H), 1.61 d, J=7.2 Hz, 1H), 1.21 (s, 18/5H), 1.07 (s, 27/5H).

REFERENCE EXAMPLE 8

N-t-butoxycarbonyl-N-[3-(4-methoxymethyloxybutyl)pyridin-4-yl]-2-naphythylpropanamide

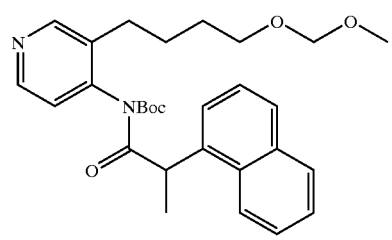

To a solution of the compound prepared in Reference example 7 (275 mg) in methanol (3.7 ml), 10% palladium carbon (27.5 mng) was added under an atmosphere of argon. The mixture was stirred for 4 hours at room temperature under an atmosphere of hydrogen gas. The reaction mixture was replaced with argon and was filtered through celite (registered trademark), the filtrate was concentrated to give the title compound (276 mg) having the following physical data.

TLC: Rf 0.49 (n-hexane:ethyl acetate=1:1);

NMR(300 MHz, CDCl$_3$): δ8.49 (s, 1/2H), 8.45 (s, 1/2H), 8.42 (d, J=5.1 Hz, 1/2H), 8.35 (d, J=5.1 Hz, 1/2H), 8.17–8.08 (m, 2/2H), 7.86 (brd, J=6.6 Hz, 2/2H), 7.78 (brd, 8.1 Hz, 2/2H), 7.59–7.39 (m, 8/2H), 6.83 (d, J=5.4 Hz, 1/2H), 6.75 (d, J=5.1 Hz, 1/2H), 5.84 (q, J=6.9 Hz, 1/2H), 5.78 (q, J=6.9 Hz, 1/2H), 4.61 (s, 2/2H), 4.51 (s, 2/2H), 3.52 (m, 2/2H), 3.36 (s, 3/2H), 3.30 (s, 3/2H), 3.26 (t, J=6.0 Hz, 2/2H), 2.52–2.38 (m, 2/2H), 2.14–2.02 (m, 2/2H), 1.73–1.57 (m, 8/2H), 1.23 (s, 9/2H), 1.06 (s, 9/2H).

EXAMPLE 8

N-[3-(4-hydroxybutyl)pyridin-4yl]-2-naphythylpropanamide

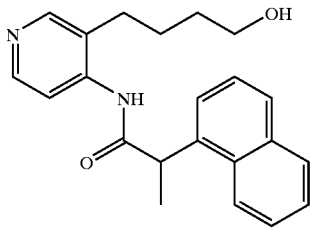

To a solution of the compound prepared in Reference example 8 (267 mg) in methanol (2.0 ml), a solution of 4N hydrochloric acid and dioxane (5.0 ml) was added, and then the mixture was stirred overnight at room temperature. The reaction mixture was concentrated to give the title compound having the following physical data.

TLC: Rf 0.55 (chloroform:methanol=9:1);

NMR(300 MHz, CDCl$_3$): δ8.92 (d, J=6.6 Hz, 1H), 8.56 (dd, J=6.6 Hz, 1H), 8.50 (brs, 1H), 8.22 (brd, J=8.1 Hz, 1H), 8.00 (m, 1H), 7.92 (brd, J=8.1 Hz, 1H), 7.67–7.46 (m, 5H), 4.97 (q, J=7.2 Hz, 1H), 3.39–3.34 (m, 2H), 2.65–2.46 (m, 2H), 1.78 (d, J=7.2 Hz, 3H), 1.32–1.11 (m, 4H).

EXAMPLE 9

4-[4-[2-(1-naphthyl)propanoylamino]pyridin-3-yl]butanoic acid

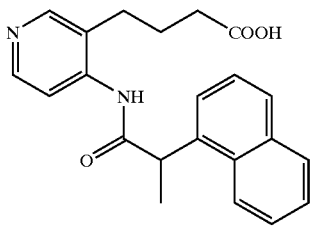

To a solution of the compound prepared in Example 8 in dimethylsulfoxide/ethyl acetate (1:1, 4 ml), triethylamine (0.45 ml) and pyridine sulfonate (258 mg) were added under cooling with ice. The mixture was stirred for 2 hours. Water was added to the reaction mixture, and the mixture was washed with ethyl acetate. The solution was neutralized by adding 1N hydrochloric acid and extracted with ethyl acetate. The organic layer was washed with a saturated aqueous solution of sodium chloride, dried over magnesium sulfate, and concentrated to obtain the oil (188 mg). A solution of the oil (178 mg) and 2-methyl-2-butene (0.5 ml) in t-butanol (10 ml), an aqueous solution(4.0 ml) of sodium chlorite (93 mg) and sodium dihydrogenphosphate (96 mg) was added, and then the mixture was stirred overnight at room temperature. The reaction mixture was concentrated. Water was added to the residue, and the mixture was extracted with chloroform. The organic layer was washed with a saturated aqueous solution of sodium chloride, dried over magnesium sulfate and concentrated to give the title compound (45 mg) having the following physical data.

TLC: Rf 0.46 (chloroform:methanol=9:1);

NMR (300 MHz, DMSO-d$_6$): δ9.62 (s, 1H), 8.33 (s, 1H), 8.32 (d, J=5.4 Hz, 1H), 8.25 (d, J=8.7 Hz, 1H), 7.94 (d, J=7.5 Hz, 1H), 7.84 (d, J=7.8 Hz, 1H), 7.77 (d, J=5.4 Hz, 1H), 7.62–7.47 (m, 4H), 4.85 (q, J=7.2 Hz, 1H), 2.62=2.56 (m, 2H), 2.11 (dd, J=7.5, 6.9 Hz, 2H), 1.61 (d, J=7.2 Hz, 3H), 1.58 (m, 1H), 1.12 (dt, J=23.7, 7.2 Hz, 1H).

REFERENCE EXAMPLE 9

N-methyl-2-nitrobenzylaminoacetic acid

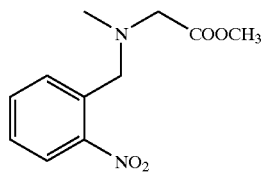

To a solution of N-methylglycine methyl ester hydrochloride (2.00 g) in methanol (20 ml), potassium hydroxide (300 mg) was added, and then the mixture was stirred for 10 minutes at room temperature. To the suspension, o-nitrobenzaldehyde (1.74 g) was added, and then the mixture was stirred overnight at room temperature. A solution of sodium cyanoborohydride (722 mg) in methanol was added to the reaction mixture, and the mixture was stirred for 4 hours at room temperature. A saturated aqueous solution of sodium bicarbonate was added to the reaction mixture, and the mixture was extracted with ethyl acetate. The organic layer was washed with water and a saturated aqueous solution of sodium chloride, dried over magnesium sulfate and concentrated. The residue was purified by column chromatography on silica gel to give the title compound (660 mg) having the following physical data.

TLC: Rf 0.24(n-hexane:ethyl acetate=4:1);

NMR(300 MHz, CDCl$_3$): δ7.84 (dd, J=8,1, 1.2 Hz, 1H), 7.68 (m, 1H), 7.56 (m, 1H), 7.40 (m, 1H), 4.04 (s, 2H), 3.71 (s, 3H), 3.33 (s, 2H), 2.37 (s, 3H).

EXAMPLE 10

N-methyl-2-[2-(1-naphthyl)propanoylamino]benzylanminoacetic acid hydrochloride

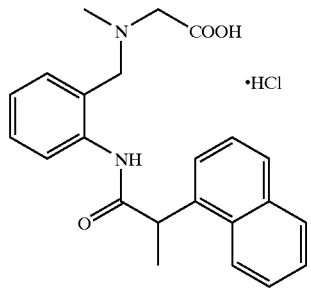

The title compound having the following physical data was obtained by the same procedure as a series of reactions of Reference example 2→Example 1→Example 2, using the compound prepared in Reference example 9.

TLC: Rf 0.20 (chloroform:methanol=9:1);

NMR(300 MHz, d$_6$-DMSO): δ10.49 (br, 1H), 10.20 (brs, 1H), 8.33 (d, J=7.8 Hz, 1H), 7.96 (d, J=7.8 Hz, 1H), 7.85 (d, J=7.8 Hz, 1H), 7.65 7.36 (m, 7H), 7.27 (m, 1H), 4.80 (q, J=6.9 Hz, 1H), 4.25 (br, 2H), 3.90 (br, 2H), 2.55 (br, 3H), 1.61 (d, J=6.9 Hz, 3H).

EXAMPLE 10(1)

2-[2-(1-naphthyl)propanoylamino]benzylaminoacetic acid hydrochloride

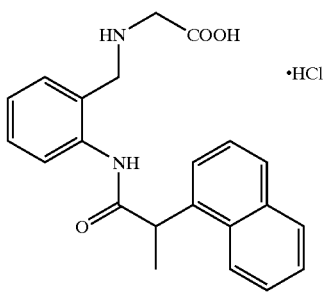

The title compound having the following physical data was obtained by the same procedure as a series of reactions of Reference example 9→Example 10, using a corresponding compound.

TLC: Rf 0.21 (chloroform:methanol=4:1);

NMR(300 MHz, $d_6$-DMSO): δ10.13 (brs, 1H), 9.40 (br, 2H), 8.32 (d, J=8.1 Hz, 1H), 7.96 (d, J=8.1 Hz, 1H), 7.85 (d, J=8.1 Hz, 1H), 7.65 7.48 (m, 5H), 7.40 (m, 1H), 7.35 7.25 (m, 2H), 4.76 (q, J=7.2 Hz, 1H), 4.04 (brs, 2H), 3.74 (brs, 2H), 1.62 (d, J=7.2 Hz, 3H).

EXAMPLE 11

4-[4-cyano-2-[2-(1-naphthyl)propanoylamino]phenyl]butanoic acid (2-hydroxy)ethyl ester

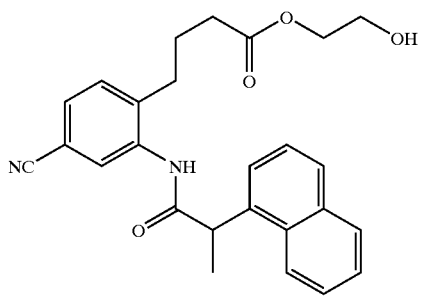

To a solution of the compound prepared in Example 2(6) (150 mg) and 2-iodoethanol (100 mg) in DMF (2 ml), potassium carbonate (65 mg) was added under an atmosphere of argon. The mixture was stirred for overnight at room temperature. Water was added to the reaction mixture, and then the mixture was extracted with ethyl acetate. The organic layer was washed with water and a saturated aqueous solution of sodium chloride, dried over and concentrated to give the crude crystal. The crude crystal was recrystallized with ethyl acetate/hexane to give the title compound (95 mg) having the following physical data.

EXAMPLE 11(1)-11(4)

The following compounds were obtained by the same procedure as a reaction of Example 11, using the compound prepared in Example 2(6) and a corresponding compound instead of 2-iodoethanol.

EXAMPLE 11(1)

4-[4-cyano-2-[2-(1-naphthyl)propanoylamino]phenyl]butanoic acid diethylaminocarbonyl methyl ester

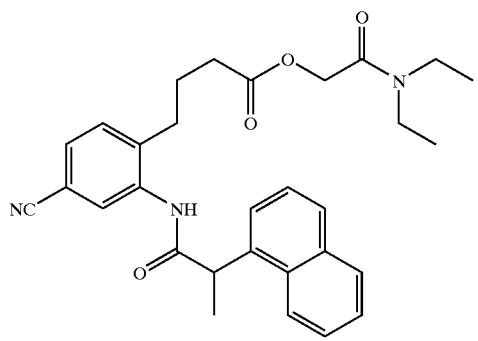

TLC: Rf 0.74 (ethyl acetate);

NMR(300 MHz, CDCl$_3$): δ8.40 (brs, 1H), 8.18 8.08 (m, 2H), 7.90 (m, 1H), 7.82 (d, J=8.1 Hz, 1H), 7.62 (m, 1H), 7.56 7.47 (m, 3H), 7.27 (dd, J=7.8, 1.5 Hz, 1H), 7.15 (d, J=7.8 Hz, 1H), 4.64 (q, J=7.2 Hz, 1H), 4.61 (d, J=14.4 Hz, 1H), 4.33 (d, J=14.4 Hz, 1H), 3.32 (m, 2H), 3.16 (m, 2H), 2.33 (m, 2H), 2.20 (t, J=6.6 Hz, 2H), 1.78 (d, J=7.2 Hz, 3H), 1.52 (m, 2H), 1.17 (t, J=7.2 Hz 3H), 1.08 (t, J=7.2 Hz, 3H).

EXAMPLE 11(2)

4-[4-cyano-2-[2-(1-naphthyl)propanoylamino]phenyl]butanoic acid ethoxycarbonylmethyl ester

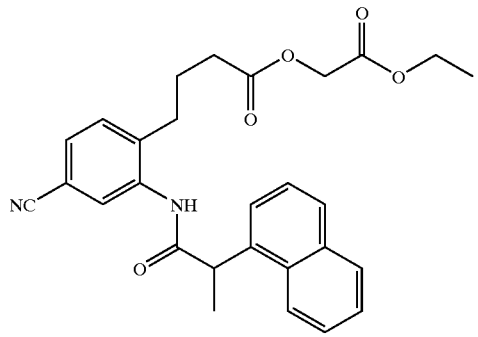

TLC: Rf 0.22 (n-hexane:ethyl acetate 3:1);

NMR(300 MHz, CDCl$_3$): δ8.45 (d, J=1.5 Hz, 1H), 8.11 (d, J=8.1 Hz, 1H), 7.91 (m, 1H), 7.85 (d, J=7.8 Hz, 1H), 7.65–7.49 (m, 5H), 7.27 (dd, J=8.1, 1.5 Hz, 1H), 7.12 (d, J=8.1 Hz, 1H), 4.64 (q, J=7.2 Hz, 1H), 4.50 (d, J=15.6 Hz, 1H), 4.44 (d, J=15.6 Hz, 1H), 4.20 (m, 2H), 2.15 (m, 4H), 1.79 (d, J=7.2 Hz, 3H), 1.38 (m, 2H), 1.28 (t, J=7.2 Hz, 3H).

EXAMPLE 11(3)

4-[4-cyano-2-[2-(1-naphthyl)propanoylamino]phenyl]butanoic acid dimethylainocarbonylmethyl ester

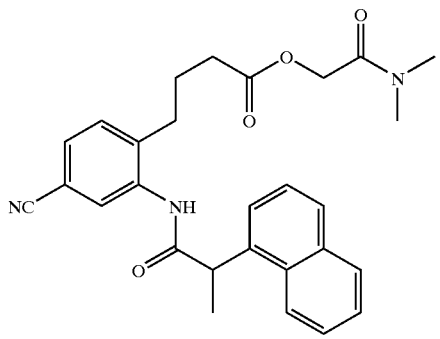

TLC: Rf 0.38 (n-hexane:ethyl acetate=1:3);

NMR(300 MHz, CDCl$_3$) δ8.42 (bs, 1H), 8.28 (bs, 1H), 8.09 (m, 1H), 7.91 (m, 1H), 7.82 (d, J=8.1 Hz, 1H), 7.64 7.47 (m, 4H), 7.28 (dd, J=8.1, 1.5 Hz, 1H), 7.16 (d, J=8.1 Hz, 1H), 4.62 (q, J=6.9 Hz, 1H) 4.61 (d, J=15.0 Hz, 1H), 4.22 (d, J=15.0 Hz, 1H), 2.83 (s, 3H), 2.81 (s, 3H), 2.41 (m, 2H), 2.22 (m, 2H), 1.75 (d, J=6.9 Hz, 3H), 1.60 (m, 2H).

EXAMPLE 11(4)

4-[4-cyano-2-[2-(1-naphthyl)propanoylamino]phenyl]butanoic acid (2-methoxy)ethyl ester

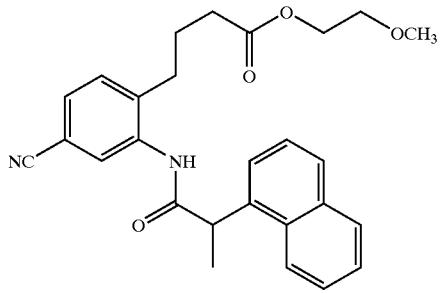

TLC: Rf 0.42 (n-hexane:ethyl acetate=1:1);

NMR(300 MHz, CDCl$_3$): δ8.50 (bs, 1H), 8.16 (m, 1H), 7.94 7.81 (m, 3H), 7.62 (d, J=7.2 Hz, 1H), 7.58 7.48 (m, 3H), 7.27 (dd, J=7.8, 1.8 Hz, 1H), 7.10 (d, J=7.8 Hz, 1H), 4.71 (q, J=7.2 Hz, 1H), 4.11 (ddd, J=12.3, 5.4, 3.6 Hz, 1H), 3.98 (ddd, J=12.3, 5.4, 3.6 Hz, 1H), 3.50 (m, 2H), 3.38 (s; 3H), 2.20 2.00 (m, 4H), 1.79 (d, J=7.2 Hz, 3H), 1.38 (m, 2H).

FORMULATION EXAMPLE 1

The following components were admixed in conventional method and punched out to obtain 100 tablets each containing 5 mg of active ingredient.

4-[2-[2-(1-naphthyl)propanoylamino]phenyl]butanoic acid . . . 500 mg
Carboxymethylcellulose calcium (disintegrating agent) . . . 200 mg
 Magnesium stearate (lubricating agent) . . . 100 mg
 Microcrystalline cellulose . . . 9.2 g

What is claimed:

1. A carboxylic acid compound of formula (I)

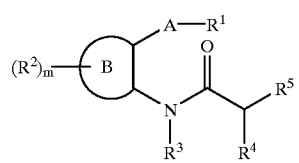

wherein R$^1$ is COOH or COOR$^6$,
R$^6$ is C1–6 alkyl, (C1–4 alkylene)—R$^{16}$,
R$^{16}$ is hydroxy, C1–4 alkoxy, COOH, C1–4 alkoxycarbonyl, CONR$^8$R$^9$,
R$^8$ and R$^9$ each independently is hydrogen or C1–4 alkyl,
A is C2–6 alkylene,
R$^2$ is C1–6 alkyl, C2–6 alkenyl, C2–6 alkynyl, C1–6 alkoxy, halogen atom, CF$_3$, cyano, nitro, hydroxy, NR$^{11}$R$^{12}$, CONR$^{11}$R$^{12}$, SO$_2$NR$^{11}$R$^{12}$, or—S(O)$_x$—(C1–6)alkyl,
m is 0, 1 or 2, when m is 2, then two R$^2$ may be same the or different,
R$^{11}$ and R$^{12}$ each independently is hydrogen or C1–4 alkyl,
x is 0, 1 or 2,
B ring is phenyl,
R$^3$ is hydrogen or C1–4 alkyl,
R$^4$ is (1) C1–8 alkyl, (2) C2–8 alkenyl, (3) C2–8 alkynyl, (4) C3–6 cycloalkyl, (5) hydroxy, (6) C1–4 alkoxy, (7) C1–4 alkoxy(C1–4)alkoxy, or (8) C1–8 alkyl substituted by 1–2 of substituents selected from halogen atom, hydroxy, C1–6 alkoxy, C1–4 alkoxy(C1–4) alkoxy, phenyl and C3–6 cycloalkyl,
R$^5$ is unsubstituted phenyl or naphthyl or phenyl or naphthyl substituted by 1–2 of R$^{13}$,
R$^{13}$ is C1–6 alkyl, C1–6 alkoxy, halogen atom, CF$_3$, cyano, C1–4 alkoxy(C1–4)alkyl, phenyl, phenyl(C1–6) alkyl, —(C1–4 alkylene)$_y$—J—(C1–8 alkylene)$_z$—R$^{14}$, benzoyl or thiophenecarbonyl and two R$^{13}$ may be the same or different,
y is 0 or 1,
z is 0 or 1,
R$^{14}$ is phenyl or pyridyl,
J is oxygen, S(O)$_t$ or NR$^{15}$,
t is 0, 1 or 2,
R$^{15}$ is hydrogen, C1–4 alkyl or acetyl;
or non-toxic salts.

2. A carboxylic acid compound of formula (I) according to the claim 1, wherein R$^1$ is COOH or COOR$^6$,
R$^6$ is C1–6 alkyl, (C1–4 alkylene)—R$^{16}$,
R$^{16}$ is hydroxy, C1–4 alkoxy, COOH, C1–4 alkoxycarbonyl, CONR$^8$R$^9$,
R$^8$ and R$^9$ each independently is hydrogen or C1–4 alkyl,
A is C2–4 alkylene,
R$^2$ is C1–6 alkyl, C2–6 alkenyl, C2–6 alkynyl, C1–6 alkoxy, halogen atom, CF$_3$ or cyano,
B ring is phenyl,
m is 0 or 1,
R$^3$ is hydrogen or C1–4 alkyl,
R$^4$ is C1–8 alkyl, C3–6 cycloalkyl or C1–8 alkyl substituted by 1–2 of C3–6 cycloalkyl, R⁵ is unsubstituted phenyl or naphthyl or phenyl or naphthyl substituted by 1–2 of $R^{13}$, $R^{13}$ is C1–6 alkyl, C1–6 alkoxy, halogen atom, $CF_3$, cyano or —(C1–4 alkylene)$_y$—J—(C1–8 alkylene)$_z$—$R^{14}$, y is 0, J is oxygen, z is 1, $R^{14}$ is phenyl;

or non-toxic salts thereof.

3. A carboxylic acid compound of formula (I) according to the claim 1 selected from (1) 4-[2-[2-(1-naphthyl)propanoylamino]phenyl]butanoic acid methyl ester, (2) 4-[4-cyano-2-[2-(1-naphthyl)propanoylamino]phenyl]butanoic acid methyl ester, (3) 4-[4-cyano-2-[2-(1-naphthyl)propanoylamino]phenyl]butanoic acid butyl ester, (4) 4-[2-[2-(1-naphthyl)propanoylamino]phenyl]butanoic acid, (5) 4-[2-[2-(4-pentylphenyl)propanoylamino]phenyl]butanoic acid, (6) 4-[2-[2-[4-(2-phenylethoxy)phenyl]propanoylamino]phenyl]butanoic acid, (7) 4-[4-cyano-2-[3-cyclopropyl-2-(1-naphthyl)propanoylamino]phenyl]butanoic acid, (8) 4-[2-[3-cyclopropyl-2-(1-naphthyl)propanoylamino]phenyl]butanoic acid, (9) 4-[4-cyano-2-[4-methyl-2-(1-naphthyl)pentanoylamino]phenyl]butanoic acid,

(10) 4-[4-cyano-2-[2-(1-naphthyl)propanoylamino]phenyl]butanoic acid,

(11) 4-[4-fluoro-2-[2-(1-naphthyl)propanoylamino]phenyl]butanoic acid,

(12) 4-[4-chloro-2-[2-(1-naphthyl)propanoylamino]phenyl]butanoic acid,

(13) 4-[4-methyl-2-[2-(1-naphthyl)propanoylamino]phenyl]butanoic acid,

(14) 4-[4-cyano-2-[2-(4-methyl-1-naphthyl)propanoylamino]phenyl]butanoic acid,

(16) 4-[4-cyano-2-[2-(4-methoxy-1-naphthyl)propanoylamino]phenyl]butanoic acid,

(17) 4-[4-ethynyl-2-[2-(1-naphthyl)propanoylamino]phenyl]butanoic acid,

(19) 4-[4-cyano-2-[2-(4-fluoro-1-naphthyl)propanoylamino]phenyl]butanoic acid,

(20) 4-[4-cyano-2-[2(R)-(1-naphthyl)propanoylamino]phenyl]butanoic acid,

(21) 4-[5-cyano-2-[2-(1-naphthyl)propanoylamino]phenyl]butanoic acid,

(22) 5-[4-cyano-2-[2-(1-naphthyl)propanoylamino]phenyl]pentanoic acid,

(23) 3-[4-cyano-2-[2-(1-naphthyl)propanoylamino]phenyl]propionic acid,

(24) 3-[4-cyano-2-[4-methyl-2-(1-naphthyl)pentanoylamino]phenyl]propionic acid,

(26) 4-[4-cyano-2-[2-(2-methyl-1-naphthyl)propanoylamino]phenyl]butanoic acid,

(27) 4-[4-cyano-2-[2-(2-methoxy-1-naphthyl)propanoylamino]phenyl]butanoic acid,

(29) 4-[4-cyano-2-[2-(1-naphthyl)propanoylamino]phenyl]butanol,

(30) N-[4-[2-[2-(1-naphthyl)propanoylamino]phenyl]butanoyl]-(3,5-dimethylisoxazol-4-γl)sulfonamide,

(33) 2-[2-(1-naphthyl)propanoylamino]benzylthioacetic acid,

(35) 4-cyano-2-[4-methyl-2-(1-naphthyl)pentanoylamino]phenyloxyacetic acid ethyl ester,

(36) 4-cyano-2-[4-methyl-2-(1-naphthyl)pentanoylamino]phenyloxyacetic acid,

(38) N-[3-(4-hydroxybutyl)pyridin-4-γl]-2-naphythylpropanamide,

(39) 4-[4-[2-(1-naphthyl)propanoylamino]pyridin-3-γl]butanoic acid,

(42) 4-[4-cyano-2-[2-(1-naphthyl)propanoylamino]phenyl]butanoic acid (2-hydroxy)ethyl ester,

(43) 4-[4-cyano-2-[2-(1-naphthyl)propanoylamino]phenyl]butanoic acid diethylaminocarbonyl methyl ester,

(44) 4-[4-cyano-2-[2-(1-naphthyl)propanoylamino]phenyl]butanoic acid ethoxycarbonylmethyl ester,

(45) 4-[4-cyano-2-[2-(1-naphthyl)propanoylamino]phenyl]butanoic acid dimethylaminocarbonylmethyl ester, and

(46) 4-[4-cyano-2-[2-(1-naphthyl)propanoylamino]phenyl]butanoic acid (2-methoxy)ethyl ester or non-toxic salts thereof.

4. A pharmaceutical composition having an activity of Prostaglandin $E_2$ receptor antagonist, which comprises a carboxylic acid comnound of formula (I) according to the claim 1 or non-toxic salts thereof as active ingredients.

5. A pharmaceutical composition according to claim 4, wherein Prostaglandin $E_2$ receptors are $EP_3$, $EP_4$, or $EP_3$ and $EP_4$.

* * * * *